(12) United States Patent
Bayahya et al.

(10) Patent No.: US 11,250,723 B1
(45) Date of Patent: Feb. 15, 2022

(54) VISUOSPATIAL DISORDERS DETECTION IN DEMENTIA USING A COMPUTER-GENERATED ENVIRONMENT BASED ON VOTING APPROACH OF MACHINE LEARNING ALGORITHMS

(71) Applicant: King Abdulaziz University, Jeddah (SA)

(72) Inventors: Areej Yahya Omar Bayahya, Jeddah (SA); Wadee Saleh Alhalabi, Jeddah (SA); Sultan Hassan Alamri, Jeddah (SA)

(73) Assignee: King Abdulaziz University, Jeddah (SA)

( * ) Notice: Subject to any disclaimer, the term of this patent is extended or adjusted under 35 U.S.C. 154(b) by 8 days.

(21) Appl. No.: 17/088,891

(22) Filed: Nov. 4, 2020

(51) Int. Cl.
| | | |
|---|---|---|
| G09B 19/00 | (2006.01) | |
| A61B 5/00 | (2006.01) | |
| G06F 3/0481 | (2013.01) | |
| G16H 50/20 | (2018.01) | |
| G16H 20/30 | (2018.01) | |
| G06F 3/04815 | (2022.01) | |

(52) U.S. Cl.
CPC ............ *G09B 19/00* (2013.01); *A61B 5/4088* (2013.01); *A61B 5/7267* (2013.01); *A61B 5/7275* (2013.01); *G06F 3/04815* (2013.01); *G16H 20/30* (2018.01); *G16H 50/20* (2018.01)

(58) Field of Classification Search
CPC ........ G16H 50/30; G16H 50/70; G16H 50/20; G16H 20/30; G06N 20/00; G06N 20/20; G06F 3/04815
See application file for complete search history.

(56) References Cited

U.S. PATENT DOCUMENTS

| | | | | |
|---|---|---|---|---|
| 7,827,123 | B1* | 11/2010 | Yagnik | G06N 20/00 |
| | | | | 706/12 |
| 9,940,844 | B2* | 4/2018 | Gazzaley | G09B 7/02 |
| 10,332,315 | B2* | 6/2019 | Samec | A61B 5/6803 |
| 10,559,221 | B2* | 2/2020 | Martucci | A61B 5/4848 |
| 10,559,386 | B1* | 2/2020 | Neumann | G06N 7/005 |
| 10,672,292 | B2* | 6/2020 | de Villers-Sidani | G09B 19/00 |
| 10,685,748 | B1* | 6/2020 | Chappell | G06F 21/32 |
| 10,719,992 | B2* | 7/2020 | Samec | A61B 5/4088 |
| 10,832,822 | B1* | 11/2020 | Neumann | G16H 70/20 |
| 10,896,756 | B2* | 1/2021 | Cook | G06F 19/00 |
| 2008/0208072 | A1* | 8/2008 | Fadem | A61B 5/726 |
| | | | | 600/544 |
| 2009/0054740 | A1* | 2/2009 | Gudmundsson | G16H 50/70 |
| | | | | 600/300 |

(Continued)

OTHER PUBLICATIONS

Sagi, O., Rokach, L. (2018). Ensemble learning: Asurvey. Wiley Interdisciplinary Reviews: Data Mining and Knowledge Discovery, 8(4). doi:10.1002/widm.1249 (Year: 2018).*

(Continued)

*Primary Examiner* — Jerry-Daryl Fletcher
*Assistant Examiner* — Daniel E Lane
(74) *Attorney, Agent, or Firm* — W&C IP

(57) ABSTRACT

A system and methodology combines virtual reality (VR) with a plurality of machine learning analyses, and uses majority voting to detect dementia and the diseases under dementia. The accuracy of the classification in the Medical Visuospatial Dementia test is very high.

6 Claims, 16 Drawing Sheets

(56) References Cited

U.S. PATENT DOCUMENTS

| | | | |
|---|---|---|---|
| 2009/0220429 A1* | 9/2009 | Johnsen | A61B 5/7267 |
| | | | 424/9.3 |
| 2014/0370479 A1* | 12/2014 | Gazzaley | A61B 5/168 |
| | | | 434/322 |
| 2016/0230227 A1* | 8/2016 | Sproul | G01N 33/6896 |
| 2016/0262680 A1* | 9/2016 | Martucci | A61B 5/4833 |
| 2016/0314255 A1* | 10/2016 | Cook | G06N 20/00 |
| 2017/0098385 A1* | 4/2017 | Martucci | G16H 30/40 |
| 2017/0229037 A1* | 8/2017 | Gazzaley | A61B 5/165 |
| 2017/0249434 A1* | 8/2017 | Brunner | G06F 16/3334 |
| 2017/0365101 A1* | 12/2017 | Samec | A61B 5/4088 |
| 2018/0146879 A9* | 5/2018 | Fadem | A61B 5/38 |
| 2018/0172694 A1* | 6/2018 | Farokhzad | G01N 33/54346 |
| 2018/0261115 A1* | 9/2018 | Gazzaley | H04L 67/10 |
| 2019/0159715 A1* | 5/2019 | Ramanathan | A61B 5/055 |
| 2019/0167179 A1* | 6/2019 | Arzy | A61B 5/7264 |
| 2019/0287309 A1* | 9/2019 | Samec | A61B 5/4094 |
| 2019/0371028 A1* | 12/2019 | Harrises | G06T 11/60 |
| 2020/0160032 A1* | 5/2020 | Allen | G06N 3/0454 |
| 2020/0312038 A1* | 10/2020 | Samec | A61B 5/4082 |
| 2020/0320132 A1* | 10/2020 | Neumann | G06N 3/08 |
| 2020/0321112 A1* | 10/2020 | Neumann | G06N 20/00 |
| 2020/0321113 A1* | 10/2020 | Neumann | G16H 15/00 |
| 2020/0321114 A1* | 10/2020 | Neumann | G16H 20/30 |
| 2020/0321115 A1* | 10/2020 | Neumann | G16H 20/60 |
| 2020/0321116 A1* | 10/2020 | Neumann | G16H 20/10 |
| 2020/0321119 A1* | 10/2020 | Neumann | G16B 50/30 |
| 2020/0321120 A1* | 10/2020 | Neumann | G06N 20/20 |
| 2020/0321121 A1* | 10/2020 | Neumann | G06N 20/20 |
| 2020/0321122 A1* | 10/2020 | Neumann | G06N 20/20 |
| 2020/0321123 A1* | 10/2020 | Neumann | G16H 50/20 |
| 2020/0327882 A1* | 10/2020 | Vairavan | G06N 20/10 |
| 2020/0356864 A1* | 11/2020 | Neumann | G06N 3/088 |
| 2020/0365051 A1* | 11/2020 | de Villers-Sidani | G16H 20/70 |
| 2020/0380421 A1* | 12/2020 | Neumann | G06N 5/04 |

OTHER PUBLICATIONS

Geron Aurelien. (2017). Hands-on machine learning with Scikit-Learn and TensorFlow: concepts, tools, and techniques to build intelligent systems. O'Reilly. (Year: 2017).*

James: "Majority Vote Classifiers: Theory and Applications", May 1998.

* cited by examiner

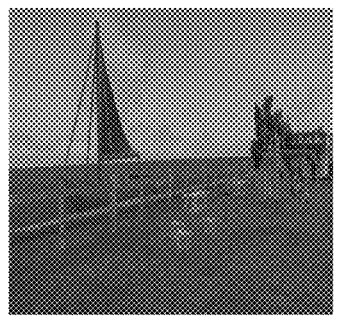  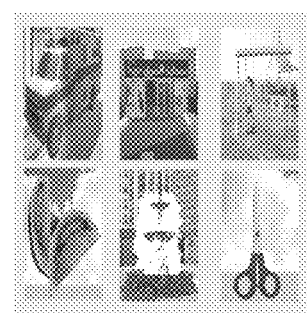
FIGURE 3A  FIGURE 3B  FIGURE 3C
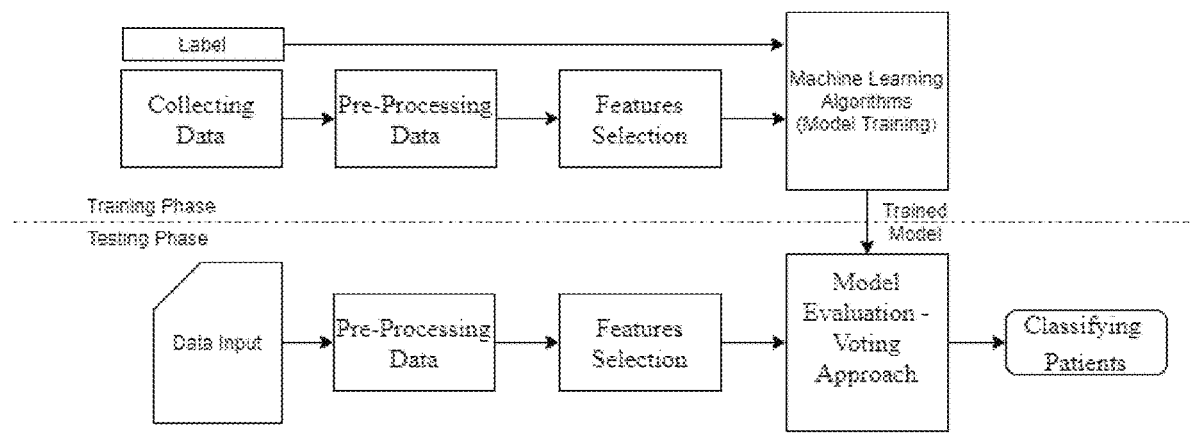
FIGURE 4

| SVC | | | | Extra Trees | | | |
|---|---|---|---|---|---|---|---|
| | Predicted Number of Class | | | | Predicted Number of Class | | |
| | Normal (0) | Dement. (1) | MCI (2) | | Normal (0) | Dement. (1) | MCI (2) |
| Normal (0) | 25 | 0 | 0 | Normal (0) | 24 | | 0 |
| Dement. (1) | 0 | 4 | 0 | Dement. (1) | 0 | 4 | 0 |
| MCI (2) | 1 | 0 | 6 | MCI (2) | 0 | 0 | 6 |

| Multinomial NB | | | | Ada Boost | | | |
|---|---|---|---|---|---|---|---|
| | Predicted Number of Class | | | | Predicted Number of Class | | |
| | Normal (0) | Dement. (1) | MCI (2) | | Normal (0) | Dement. (1) | MCI (2) |
| Normal (0) | 24 | 0 | | Normal (0) | 24 | 0 | 1 |
| Dement. (1) | 0 | 4 | 0 | Dement. (1) | 0 | 4 | 0 |
| MCI (2) | 2 | 0 | 5 | MCI (2) | 0 | 0 | 7 |

| K-Neighbors | | | | MLP | | | |
|---|---|---|---|---|---|---|---|
| | Predicted Number of Class | | | | Predicted Number of Class | | |
| | Normal (0) | Dement. (1) | MCI (2) | | Normal (0) | Dement. (1) | MCI (2) |
| Normal (0) | 24 | 0 | | Normal (0) | 25 | 0 | 0 |
| Dement. (1) | 0 | 4 | 0 | Dement. (1) | 0 | 4 | 0 |
| MCI (2) | 1 | 0 | 6 | MCI (2) | 1 | 0 | 6 |

| Gradient Boosting | | | | XGB | | | |
|---|---|---|---|---|---|---|---|
| | Predicted Number of Class | | | | Predicted Number of Class | | |
| | Normal (0) | Dement. (1) | MCI (2) | | Normal (0) | Dement. (1) | MCI (2) |
| Normal (0) | 24 | 0 | 1 | Normal (0) | 25 | 0 | 0 |
| Dement. (1) | 0 | 4 | 0 | Dement. (1) | 0 | 4 | 0 |
| MCI (2) | 0 | 0 | 7 | MCI (2) | 2 | 0 | 5 |

| Random Forest | | | | Decision Tree | | | |
|---|---|---|---|---|---|---|---|
| | Predicted Number of Class | | | | Predicted Number of Class | | |
| | Normal (0) | Dement. (1) | MCI (2) | | Normal (0) | Dement. (1) | MCI (2) |
| Normal (0) | 25 | 0 | 0 | Normal (0) | 25 | 0 | 0 |
| Dement. (1) | 0 | 4 | 0 | Dement. (1) | 0 | 4 | 0 |
| MCI (2) | 2 | 0 | 5 | MCI (2) | 1 | 0 | 6 |

FIGURE 6

VISUOSPATIAL DISORDERS DETECTION IN DEMENTIA USING A COMPUTER-GENERATED ENVIRONMENT BASED ON VOTING APPROACH OF MACHINE LEARNING ALGORITHMS

FIELD OF THE INVENTION

The invention is generally related to dementia testing, and is particularly related to a computer based test referred to as a Medical Visuospatial Dementia Test (referred to as "MVD Test") which is used to detect demented patients and to classify the subject into one of three different categories (Normal, demented, MCI) using a majority voting approach of machine learning algorithms. The MVD test takes 5 to 7 minutes to diagnose patients. In addition, the MVD test classifies any new patient or participant using the majority voting approach of machine learning algorithms.

BACKGROUND

Today, diagnosis of diseases is a serious task where importance comes from understanding its mechanisms and symptoms through clinical examination and assessment.

One of these diseases is dementia. According to the National Institutes of Health [1], dementia is not a specific disease whereas it is a descriptive term of defects in human brain, which leads to a collection of symptoms of neurocognitive dysfunction [1]. In addition to age, the strongest risk factors for dementia include chronic health conditions such as hypertension and diabetes, unhealthy lifestyle such as smoking, and family history [1]. Dementia is rapidly progressive and, in a span of less than two years, can advance from the first symptoms to the next stage. The symptoms of disease appear as forgetting appointments, getting lost, impairment in receiving and recalling new information, having impaired visuospatial skills, poor judgment such as trouble managing finances, having impaired language function, behavior changes such as social withdrawal and failure in usual activities such as making coffee and driving a car, etc. [1]. The different types and issues connected to Dementia are: Alzheimer's Disease (AD), Vascular Dementia (VaD), Dementia with Lewy Bodies (DLB), Frontotemporal Lobar Degeneration (FTLD), Mixed Dementia (MD), Parkinson's Disease (PD) Dementia, Creutzfeldt-Jakob disease and Normal Pressure Hydrocephalus [2].

The detection methods of cognitive impairment are classified into two classes: cognitive and non-cognitive tests (see FIG. 1) [3]. Cognitive tests are procedures based on measuring the patient's cognition through the use of questions, tasks, and problem-solving activities. These procedures are considered non-invasive methods. They are easy to implement, accurate, and harmless [3]. The non-cognitive test can be considered using any of the other methods available, invasive as well as non-invasive. The invasive methods depend on information and data taken from inside the human body through procedures such as blood extraction, surgery and drug treatments (see FIG. 1). The non-invasive methods are medical procedures not requiring the introduction of instruments into the body. It is suitable for the majority of patients [3]. For example, AD requires several stages to be diagnosed, and the stage of diagnosis can include both cognitive and non-cognitive methods. Accordingly, most studies are conducted on non-cognitive methods [2, 4-6] concurrently with a cognitive test [7-9].

For the detection of dementia, the cognitive functions need to be assessed. There are several domains that have an effect on the neurocognitive brain. The cognitive functions include: visuospatial disorientation, complex attention, executive function, learning and memory, language, perceptual-motor, or social cognition [1].

Visuospatial disorientation is known as a topographical disorder, visuospatial disorder, or wayfinding difficulty [10]. Visuospatial processing is the ability to know the presence and distance to things in the surrounding space [11]. Tue et al. [12] pointed out that in the clinic practice, there is a limited diagnosis of spatial orientation problems. This is due to lack of feasible and proper practical tasks in a clinical setting. The same researchers [12] noted that the results of orientation performance were complementary to episodic memory measurement methods. This led to the diagnosis accuracy improvement for patients with Alzheimer's and a behavioural variant of FTD (Frontotemporal Dementia), known as vbFTD (Behavioral Variant Frontotemporal Dementia). These studies also demonstrated the relationship of spatial deficit to dementia by applying visuospatial domain to test the cognitive impairment of dementia patients [10, 13, 14]. Pal et al. [13] demonstrated visuospatial task dysfunction in patients with dementia, especially in AD, FTD, VaD and DLB.

Mohr et al. [14] confirmed the existence of equivalent degrees of overall cognitive dysfunction for both Parkinson's and Alzheimer's patients; in addition, visuospatial function dissociated from memory showed a defect in both groups of patients. Yamada et al. [10] observed the problem of visuospatial disorientation in patients with mixed dementia by monitoring the problems of wandering and large urine spills in the bathroom. Cognitive tests based on visuospatial dysfunction for elderly reveal the symptoms of Alzheimer's disease for up to five years before the onset of other symptoms, including memory impairment [11].

Memory functions are performed by distributed neural networks throughout the brain [15]. Thus, memory defect is a common symptom among all types of dementia. Frisch et al. [15] assessed different memory domains (verbal, visual, forgetting rates) and different imaging markers (glucose metabolism, grey matter volume) in the whole brain. Its results showed that memory problems were associated with all dementia syndromes related to Alzheimer's patients and Frontotemporal Lobar Degeneration. Park et al. [16] observed that episodic memory is the most predominant cognitive dysfunction domain preceding the diagnosis of dementia. In addition, it was found that verbal memory is one of the most important indicators of disease progression from MCI to dementia [16].

There are multiple cognitive tests to measure cognitive function and patient's cognitions. One of these tests, which was also adopted in this study, was the Mini-Cog test. It tests two different aspects of cognitive domains: visuospatial disorientation and memory recall. Mini-Cog test is used for enhancing and validating primary care and is available in multiple languages/cultures [17]. It is useful when used in contexts where there is little or no education, language and race bias. Furthermore, it has a short administration time. The test can be used to increase detection of cognitive impairment in older adults.

Virtual reality (VR) today is growing in use with the medical field, and can be used for diagnosis of dementia disease and mild cognitive impairment. It is one of the most important computerized methods used to assess cognitive dysfunction by testing cognitive function. It addresses challenges by concentrating on navigation and orientation, cognitive functionality, and other instrumental activities of daily living (IADLs) [1]. However, in order to prove its effectiveness, VR integrated in the medical field needs high accuracy in evaluation and result. VR is already making a difference in the health care industry. It has been harnessed to provide a more appropriate and effective health care service in several health care service including assisting doctors, surgeons, physicians and nurses in—surgery, diagnosis the diseases, physical treatment, and long-term condition management. Where diagnosing disease is concerned, system smart health can offer a method of monitoring health levels or improving health outcomes at the clinic.

The idea of VR comes from vehicle simulation and teleoperations technology of the 1960s [18] and is defined as a head-referenced computer, interactive computer simulation and virtual image displays that insert users into the illusion of locomotion to another location. It is a communication channel for human-machine interaction Cognitive Methods Based Virtual Reality Investments are required in the diagnosis of AD by developing new screening tools using advanced technology. VR is a promising tool in the medical field, especially for detecting dementia and AD. It allows specialists to understand cognitive disabilities more accurately and to assess the cognitive perception of patients when the patients are practicing daily activities. Accordingly, VR can be used to mimic everyday tasks, increasing ecological validity.

Machine learning algorithms are computational methods used as data analysis techniques [19]. They are used in many fields and make critical decisions in areas such as medical diagnosis, nuclear energy, stock trading and others. These algorithms have an improved performance whenever the number of available samples of data is high [19].

Tu, Cushman, Zakzanis and Lesk [12, 20-22] discussed ways to diagnose early stages of AD to overcome the weakness of traditional tests. Most of the research focuses on two important aspects: navigational or memory processes or both. The studies that focused on the detection of cognitive impairment in spatial navigation include memory deficit and executive function.

Their VR navigation task study [20, 21, 23, 24] showed that Alzheimer's patients have damage in spatial skills. The VR navigation task and the real-world navigation task led to similar performance deficits.

Tu et al. [12] investigated spatial orientation using a novel ecological, non-immersive virtual supermarket task. Zakzanis et al. [21] created an immersed virtual city to examine age- and AD-related differences in route learning and spatial memory. They found that AD patients made more mistakes on the recognition task than others. All these studies use VR to provide a valid assessment of navigational ability.

Memory deficits may inhibit navigation within a virtual environment. Loss of memory is one of the most common symptoms of AD. Episodic memory is what people remember in everyday life and can be measured by verbal tasks, visual information, and reaction to everyday events [23]. VR offers some advantages over standard (pen-paper) assessments of spatial memory and real-world route learning tasks by recording real time data and errors made by the patient as they navigate through the virtual environment. Thus, [23] [22] focused on memory assessment to diagnose the disease. They showed a significant correlation between daily memory complaints and performance on their virtual reality test. Lesk et al. [22] developed a non-immersive virtual simulation designed to assess visuo-spatial memory, semantic memory and to investigate cognitive function. Plancher et al. [23] characterized episodic memory profiles in an ecological fashion. They focused on perceptual details and spatio-temporal contextual elements by using two immersive virtual environments. Also, that study compared the impact of active vs. passive exploration on memory performance.

The executive functions are high-level mental functions that are used to measure the severity of cognitive disorders in Alzheimer's patients. Executive functions include attention deficit, planning, problem-solving, multi-task, monitoring and behavior control. Ching Yeh et al. [8] developed an immersive virtual convenience store for assessment of the executive functions and memory. A test-taker (human assistant) recorded the interactive human-machine interface.

Machine Learning or "ML" has many types of training algorithms: supervised learning, unsupervised learning, semi-supervised learning and reinforcement learning [25]. Supervised Learning builds a model from a specific training dataset [26]. The machine learns from training data, then applies the knowledge to testing data. The data is well labelled and is already tagged with correct class. The machine already analyzes the training data, and when new data comes, it produces a correct class from labeled data [25]. Supervised Learning is classified into two categories of algorithms: classification and regression. An algorithm is called classification when the data output is categorized such as disease and no disease[25], whereas it is a regression algorithm when the data output is a real value such as dollars or weight[25].

There are some features in the ML that are useful to solving medical diagnosis tasks as follows: good performance, dealing with missing data, dealing with noisy data, transparency of diagnostic knowledge, and when diagnosing new patients [27].

The purpose of using MLA in diagnosing Alzheimer's disease is to identify new patients that have some indicators of the disease and to give high accuracy of prediction. The standard statistical analysis that used median, mean, and standard deviation is insufficient to classify any new patients [28]. Shamsuddin et al. [24] developed a novel simulation, interactive 3D based system (VREAD). It diagnosed an MCI that may convert to Alzheimer's disease over time by using data mining techniques. VREAD consisted of three modules: VR Practice, VR Park and VR Games. Each participant passes through a training phase and testing phase. It focused on Spatial Navigation and Topographical Disorientation (TD). Algorithms such as J48, Naïve Bayes, Bagging, and Feed Forward Multilayer Perceptron Neural Networks give a high accuracy (90%) prediction for the discrimination between Moderate Cognitive Impairment and healthy elderly. Relying on Machine learning in the classification and analysis, the results have greater strength, credibility and the outcomes are diagnosed faster.

There is a huge demand for the development of new tools and advanced technology to be invested in the diagnosis of Alzheimer's disease and dementia. One promising technique in the medical field, especially for diagnosing dementia, is using VR technology along with data mining technique. Table I presents a brief summary of VR based cognitive methods. There were no studies which combined a VR system and analysis of the result by machine learning algorithms with a voting approach to detect dementia and the diseases under dementia.

TABLE 1

Brief Summary of Cognitive Methods Based on Virtual Reality for AD & Dementia Diagnosis

| | | | | Interaction technique used | | | | | | | |
|---|---|---|---|---|---|---|---|---|---|---|---|
| | | | | Methodology type | | | Immersion type | | | MLA | |
| Reference | Participant | Focus feature | Assessment methods | Tasks | Games | IADL | Full | semi | No | N0 Voting | Voting |
| [21] | Young adults = 8 Older adults = 7 | Spatial navigation, spatial memory, ecological validity | Virtual City Test, California Verbal Learning Test, neuropsychological tests | √ | | | √ | | | | |
| [12] | AD = 20 FTD = 24 SD = 14 healthy Controls = 23 | Spatial translation, spatial disorientation | Navigation virtual supermarket, Addenbrooke's Cognitive Examination-Revised, Rey-Auditory Verbal Learning Test, Rey Complex-Figure Test, and Digit Span-MRI | √ | | | | | √ | | |
| [23] | HE = 21 Amnestic MCI = 15 AD = 15 | Virtual episodic memory, Long term binding, Spatial allocentric memory assessments | VR city (VR episodic memory test), Verbal memory test, neuropsychological tests. | √ | | | √ | | | | |
| [22] | HE = 22 MCI = 9 | Semantic memory, visuospatial associative memory | VR practice, VR park and VR games, Neuropsychological tests, Graded naming test, CANTAB Paired associate learning test, MMSE, Word recall, Questionnaires | √ | | | | | √ | | |
| [8] | SD = 60, H People = 30 | Executive functions and memory | virtual shopping test (memorizing a shopping list, looking for certain goods, and checking out), test-takers. | √ | √ | | √ | | | | |
| [24] | HE-22 MCI = 9 | Topographical Disorientation (TD) | VR practice, VR park and VR games, | √ | √ | | | | √ | √ | |

SUMMARY

An objective of this invention is to provide a novel cognitive tool using VR environment with Machine Learning algorithms as computer aided diagnosis (CAD) in order to diagnose various types of dementia patients. The Medical Visuospatial Dementia Test, or "MVD Test", is used to as different cognitive domains such as spatial orientation, visuospatial, memory recall and visual memory domain. After collecting scores from tasks, data is analyzed using non-parametric statistical tests and voting approach of machine learning algorithms is applied. In testing, it was found that the participants belonged to three different groups of elderly people: dementia, MCI, healthy older. Dementia and MCI can have both deficits in one or more cognitive domains; however, MCI patients are independent as is related to the activities of daily living. Several objectives were considered in the development of this invention:

To develop a VR environment along with machine learning algorithms in order to detect patients with dementia.
To develop VR environment that uses spatial and visuospatial domain that reflects the real-world conditions.
To examine patients in the early stage of dementia who have functional disabilities in their daily lives.
To compare the performance of participants who have early and moderately severe dementia, mild cognitive impairment (MCI), and older adults with normal cognitive functioning.
To create a new real patients' data using cognitive test based on virtual environment simulated to real world tasks.

The present invention relates to a method of detecting visuospatial disorders which uses data gathered from a subject's performance in a virtual reality environment to determine the subject's level of cognitive impairment.

Some aspects of the invention include a method of predicting visuospatial disorders. The method includes receiving input data for a subject as the subject performs multiple tasks in a 3D virtual environment. The multiple tasks are designed to assess the subject's performance in multiple cognitive fields. The input data is then supplied to multiple machine learning algorithms which classify the subject into one of three different levels of impairment: normal, demented, or mild cognitive impairment. The present invention uses a system of voting to produce a final classification.

The present invention may be implemented in multiple phases, such that in the first phase subjects provide information that may increase the accuracy of the machine learning algorithms. This information may include personal information, patient history, medical history, vision impairment problems, depression, past head injuries or exposure to solvents, or any clinical diagnoses. The present invention may also be used in conjunction with existing clinical tests such as Mini-cog or other pen and paper tests, diagnosis by a doctor, or evaluation of a subject's performance of daily tasks. All information provided by the subject as well as the results of any clinical tests may then be stored locally or sent to a database.

The second phase of the present invention may involve the subject being trained on the equipment and performing multiple tasks in a 3D virtual environment. The multiple tasks may be part of a novel test known as a Medical Visuospatial Dementia Test ("MVD Test") which assesses multiple cognitive domains such as spatial orientation, navigational and visuospatial skills, memory recall, or visual memory domain. For tasks configured to test navigational, spatial or visuospatial skills, some embodiments of the invention may receive as input data the movements of a subject in the 3D virtual environment. Other embodiments of the invention may receive as input data the total time a subject took to complete a certain task. For tasks configured to test memory recall or visual memory domain, some embodiments of the invention may receive as input data the number of correct and incorrect answers a subject gave. The input data may then be stored locally or sent to a database.

When the input data is collected it is then supplied to multiple machine learning algorithms to classify the subject. The multiple machine learning algorithms may include SVC Classifier, K-Neighbors Classifier, Gradient Boosting Classifier, AdaBoost Classifier, Random-Forest Classifier, XGB Classifier, ExtraTree Classifier, DecisionTree Classifier, Multinomial-NB Classifier, or MLP Classifier. Each algorithm classifies the subject into one of three categories: normal, demented, and mild cognitive impairment. The final classification is then determined by a system of voting. Various systems of voting may be used, including Ensemble Vote, which outputs as a final classification the most frequent result from all of the machine learning algorithms or the average of their scores.

DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

FIG. 3A is a picture of an exemplary virtual reality (VR) environment that a patient roams around in when executing a navigational task.

FIG. 3B is a picture of an exemplary VR environment where a patient performs a memory and delay recall task.

FIG. 3C is a picture of an exemplary VR presentation used for a patient visual memory task.

FIG. 4 is a schematic showing functionality of supervised classification.

FIG. 6 is a Confusion Matrix for Multi-categorical Classification Models.

DETAILED DESCRIPTION

Figure 1:
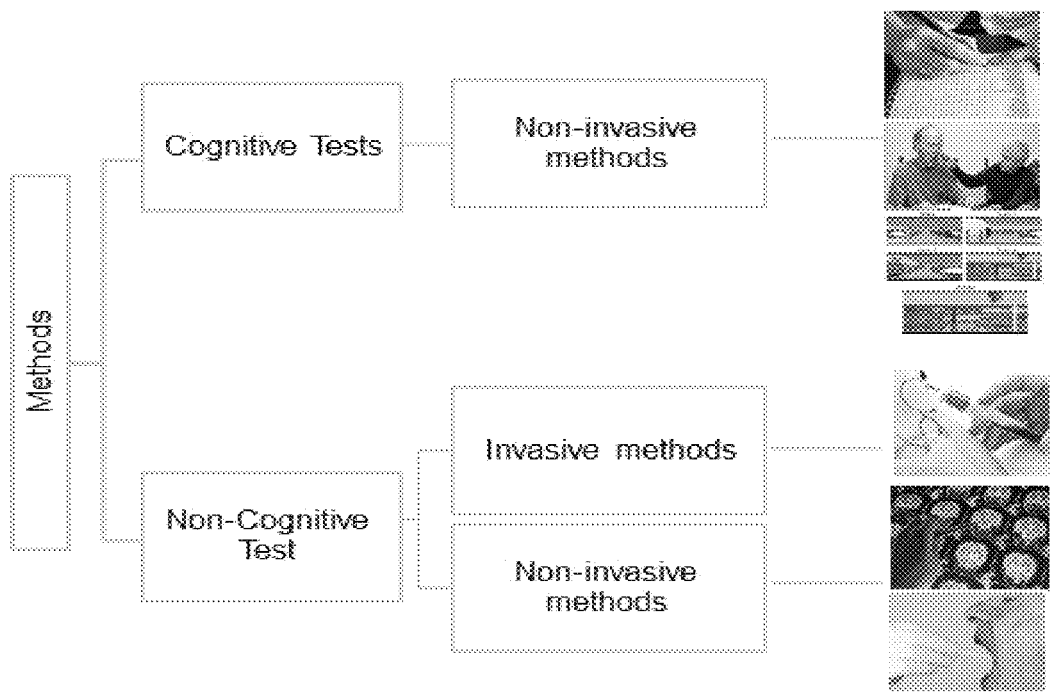
FIG. 1 is a schematic showing classification methods for to detect cognitive impairment.
Figure 2:
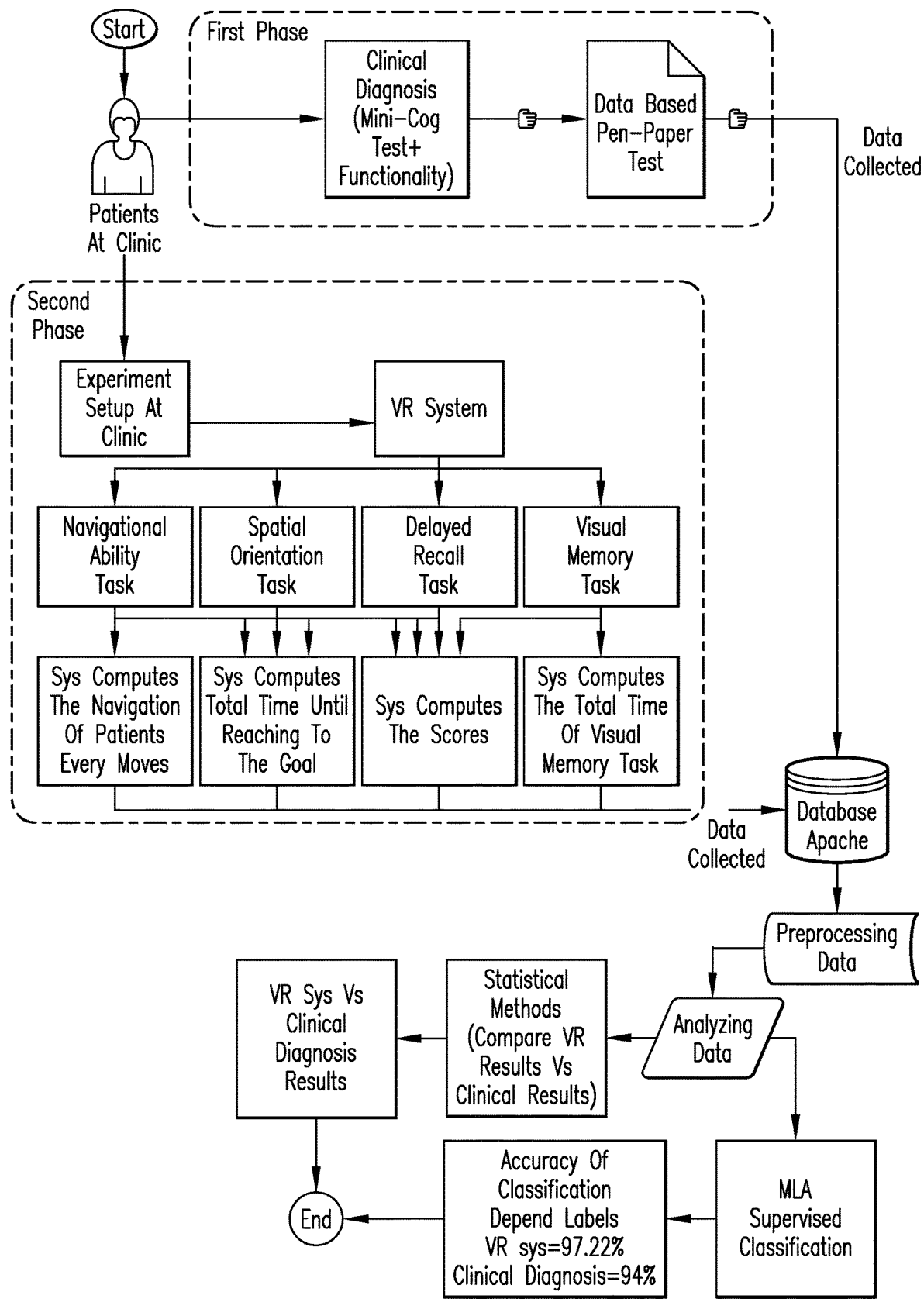
FIG. 2 is a schematic architecture model used to classify dementia patients.

In an embodiment of the invention, there is a system combining a model for patient information storage and retrieval, cognitive test-based VR System, and MLAs for classifying the patients' condition. Results obtained using this system are described below. The designed model contains different cognitive methods for measuring the impairment of patients' cognitive abilities and uses classification tools to determine whether the patient has cognitive impairment based on the data extracted from the system. This unique work combined three main parts, which are as follows: VR testing, multi-MLAs, and voting approach, and the combination makes this work unique. The performance of participants was compared with individuals diagnosis based on traditional neuropsychological tests used for the same cognitive domains: i) early and moderately severe dementia; ii) MCI; and iii) older adults who have normal cognitive. It was designed specifically for the Arabs in the Middle East, from both the educated and non-educated class, but the general operation of the system and methodology is not limited to individuals from specific geographic areas. The system was made with off-the-shelf consumer components and is designed to work in any neurology or clinical facility as a quantitative assessment of patients along with other cognitive or non-cognitive approaches. The system was tested on 115 real patients from Dr. Soliman Fakeeh Hospital, King Abdul-Aziz Hospital, International Medical Centre and Association of Elderly People Friends. Thirty of those individuals have a cognitive impairment (dementia), sixty-five are cognitively healthy, and ten have a mild cognitive impairment. The age of all patients was higher than 50 years old and they had both educated or non-educated backgrounds. The nature of the collected data is discrete, non-parametric, non-normalized, and labeled. Consequently, supervised and classification algorithms were used to classify the patients. The data is used as input for the MLAs that perform a classification at the output end. In addition, for the MLAs, a series of statistical indicators were computed: accuracy, sensitivity, precision and specificity. The architecture model used to classify dementia patients is shown in FIG. 2.

Clinical and Demographic Information

Enrollment is the first stage that is performed when using the system. This provides a record that can be used for all subsequent patients' outcome measures being generated. In the process, the Assistant/Nurse enrolls the patients by providing the following patient information to the system:
  Personal information
  Patient history and medical history
  Vision impairment problems.
  Depression, past head injuries or exposure to solvents.
  Clinical diagnosis Patients Process & Mechanism of Data Collection Firstly, the patient reaches at clinic, then, he or she goes to the first phase FIG. 2.
  At the first phase, the patient is preparing for the experiment by explaining instructions to him and training him to use the devices
  the Assistant/Nurse creates the patient's record by providing the patient information to the system. {system directly stores the information and send it to database}
  After that, the VR Test will Begin.
  During the Tasks, the system calculates the time, computes the navigation of patient every move, and computes the scores until he reaches the first destination and final destination. {system directly stores the information and send it to the database}
  Secondly, the patient receives a clinical test
  At the second phase, the doctor tests the patient based on cognitive tests (pen paper test), such as Mini-cog test.
  The doctor evaluates the patient's performance of daily tasks.
  The doctor registers the total scores on paper or records them in a computer.
  Alternatively, the doctor gives the patient's scores to the assistant, and the assistant inserts these data into the system and directly the data stores into the database.
  The database preferably has three Tables, one for Patients' history, another for patient's scores, and the last for the patient's path coordinates.
  Pre-processing and analyzing the data by statistical methods to compare VR results vs clinical results and MLA with voting approach to classify the patients and detect the disease in any new patient Visuospatial Function Visuospatial function is commonly conceptualized in three components: visual perception, construction, and visual memory [29]. The task involves detecting and localizing a point in space, detecting and judging direction and distance, and detecting topographical orientation.

Navigational Task

As depicted in FIG. 3A, the researcher or clinician applies a navigation test algorithm in a virtual environment to measure patients' navigation. Preferably an input device [a joystick] that has four directions (right, left, front, back) is used to move the avatar to the right path. In this task, the system measures two different directions: topographical orientation, and judgment of direction and distance [11]. It is one of the critical techniques for simulation system-based VR to detect dementia in early stage. The task is performed in the following steps:
  The system shows a simulation so that the patient can see the path from the start point to the destination.
  The scene returns to the starting point with instructions to guide the patient.
  The patient answers several questions to measure judgment of direction and to set points according to the answer.
  During the task, the system calculates the total time and the patient's path coordinates.

Visual Memory Task

There are two main concepts under visual memory: recall (or recognition) of visual information and topographical memory; where topographical memory includes encoding and perception of spatial orientation to walk in the surrounding environment [11]. With reference to FIG. 3B, the task is performed in the following steps:
  The system displays several images, then the patient tries to remember if they were previously shown.
  The assistant/nurse determines the patient's correct answers by the input device, then the system calculates the points.

Memory Function

Memory is the most predominant cognitive dysfunction domain preceding the diagnosis of dementia. Elements addressed by this invention are focused on memory delay recall and visual memory.

Memory Registration and Delayed Recall Task

To measure memory deficits in patients with dementia we used the three words recall algorithm [30]. It allows the patients to use the natural and intuitive way to measure the level of memory deficit. With reference to FIG. 3C, the task is performed in the following steps:
  The system asks the patient to repeat three words and focus on them in registration stage.
  The patient navigates in the VE to reach the y-place, then the system asks the patient to pronounce the previous three words
  The assistant/nurse determines the patient's correct answers by the input device, then the system calculates the points.

Outcomes Measurements

A number of factors are calculated to detect cognitive impairment in the patients: time to completion, accomplishment VR score, patients' history, and neuropsychological assessment.
  Amount of times they changed direction, the total time they took to arrive to their destination were recorded; and total time they took to finish the visual memory task
  VR scores include: navigational ability, spatial orientation, memory recall, visual memory correct, and visual memory incorrect.

Machine Learning Algorithms

Machine Learning Algorithms (MLA) learn the relationships between different input data for patients such as (test scores, time spent, etc.). The classification of patients depends on outcome data from each patient. In this work, these algorithms are used to classify patients into three classes: i) cognitive impairment (dementia); ii) cognitively healthy older adult; and iii) mild cognitive impairment. However, the system has more than one MLA to vote by majority voting approach for a higher rating and gives reliable information, high accuracy in the diagnosis and classification of patients.

As shown in FIG. 4, a feature selection approach is used to choose the most important features. These feature sets capture the basic information about each input. Then, feature sets and labels are fed into the machine learning algorithm to generate a model. During the testing phase, the same feature is used with a new data. These feature sets are then fed into the model, which generates predicted labels. Finally, the results of all methods are then fed into voting approach technique as majority voting to predict final label of patient.

Classification Process

Classification is the task of identifying and sorting the objects from certain groups into their appropriate categories by building a model based on one or more numerical and/or categorical variables (predictors or attributes). The goal of classification is to be predictable for each data accurately and correctly [31]. The main idea of classification is to build by identifying the objects in certain groups and assigning to their appropriate categories—predictors or attributes [26].

In various aspects of the invention, classification methods were performed where classifying patients depends on multiple algorithms i.e. Decision Tree [32], Extra Trees [33], AdaBoost [34], XGB [35], Gradient Boosting [36], SVC [37], RANDOM FOREST® [38], Multinomial NB [39, 40], K-Neighbors [41], and MLP [42]. These algorithms are used for disease diagnosis as they led to good accuracy. After that, a voting approach namely Ensemble Vote [43, 44] are used to vote the most frequently used from the latter MLAs. The next paragraphs will discuss the classification methods that were applied.

Decision Trees Classifier

A Decision Tree Classifier is defined as a multistage classification strategy, which is a classifier expressed as a recursive partition of the instant space [45]. It is an attribute-vector approach, and can be applied to the tree, leaf node of the tree labeled with a class, or a structure containing a test. The classification process is completed by performing the test onto the attributes, reaching one or another leaf. The Decision Tree Classifier builds hyperplanes/partitions to divide the space between the classes [45].

Extra Trees Classifier

The Extremely Randomized Trees Classifier is an extremely randomized version of the Decision Tree Classifier, and is a type of ensemble supervised learning technique that fits a number of randomized decision trees [33]. It is used for improving the predictive accuracy by using the average of the data within a dataset. It is very similar to a RANDOM FOREST® Classifier but differs in the construction of the decision trees.

AdaBoost Classifier

Introduced in 1995 by Freund and Schapire [34], the principle of AdaBoost is to fit a sequence of weak learners where the predictions are combined through a weighted majority vote to produce the final prediction [36]. AdaBoost can be used for multi-class classification.

Gradient Boosting Classifier

This classifier is used for classification tasks and supports both binary and multi-class classification. It creates a strong predictive model from combining many weak learning models together [36], and is used to reduce the loss between the training actual class and the predicted class value.

XGB Classifier

This classifier is a system optimization that is a customized version of the Gradient Boosting Decision Tree system. It is a tool used to push the extreme of the computation limits of what is possible for gradient boosting algorithms to provide a portable, scalable, and accurate library [35].

RANDOM FOREST® Classifier

RANDOM FOREST® Classifier is an ensemble algorithm that consists of a large number of relatively uncorrelated models (trees) [46]. A class prediction comes from each individual tree in the random forest. Then, the most votes of the class becomes our model's prediction [46].

Multinomial Naive Bayes (NB)

Multinomial Naive Bayes is a uni-gram language model with integer word counts [39]. It is an appropriate distribution when the data consists of counts [39]. It should be used for the features with discrete values like 1,2,3. This approach has also been used for text classification.

Support Vector Classifier (SVC)

The most applicable machine learning algorithm is Support Vector Classifier. It builds an optimal hyperplane which is used for linearly separable patterns [37]. The optimal hyperplane is elected after fitting the data and returning the best fit hyperplane for classifying patterns [47].

K-Neighbors Classifier

This is a non-parametric method used for either classification or regression. The data is classified by voting the K-closest neighbors training in the feature space [41]. To find the closest similar points, the distance between points can be determined by using distance measures such as Manhattan distance, Euclidean distance, etc. [41]. The prediction comes from the most votes of each object for their class. The models will be generated with no requirement for training data points.

Multilayer Perceptron

Multilayer Perceptron is a classical type of neural network. MLPs are suitable for classification prediction because they are capable of mapping highly non-linear relations between inputs and outputs and provide a good performance [42].

Generalize MLA Results Using Voting Approach

Figure 5:
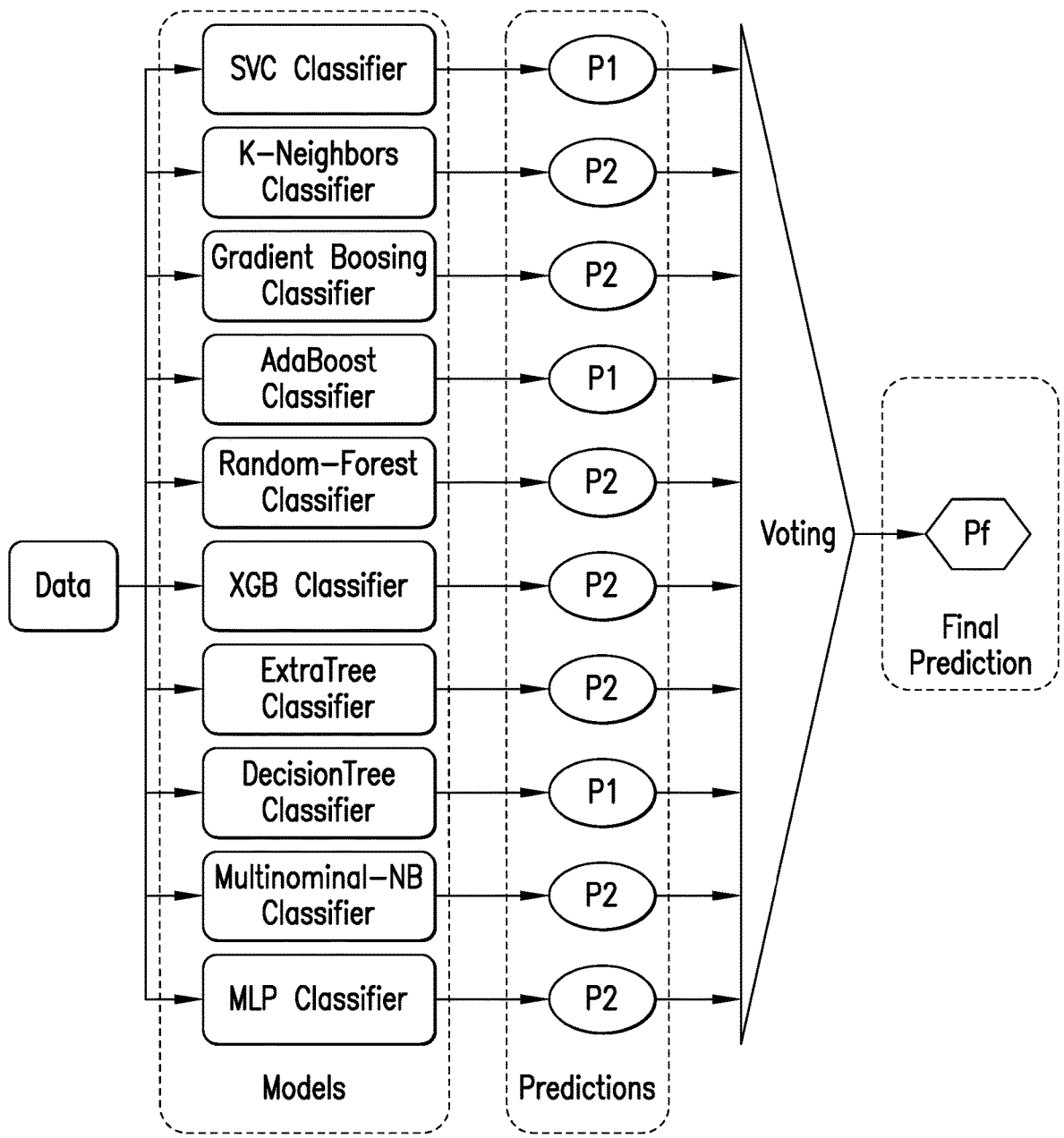
FIG. 5 is a schematic of a Voting Approach as Majority Voting using Ensemble Vote Algorithm.
Figure 7A:
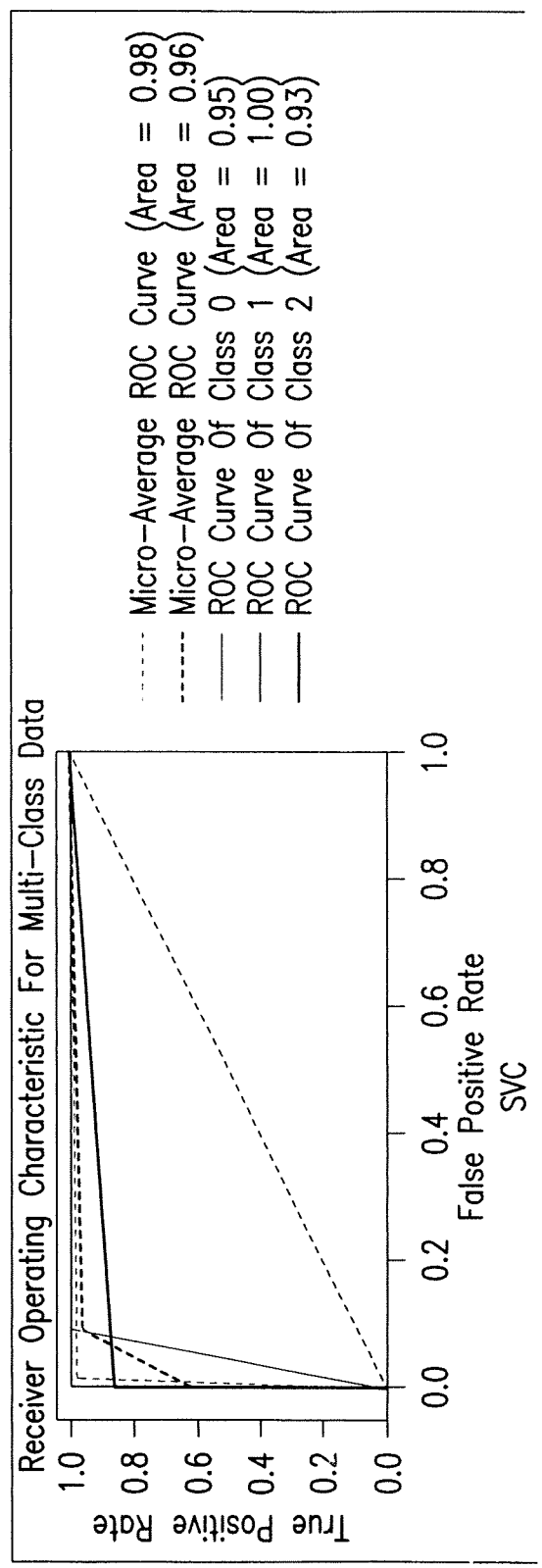
FIG. 7A is a graph showing Receiver Operating Characteristic (ROC) Curve Analysis of the SVC algorithm.
Figure 7B:
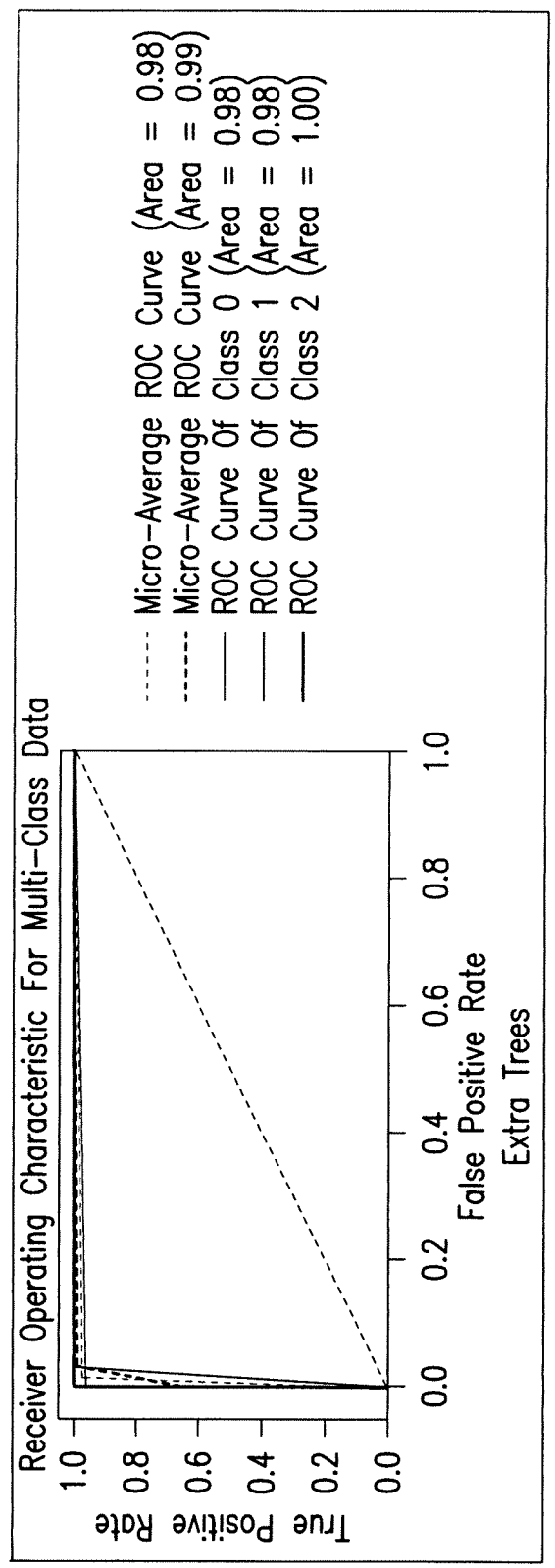
FIG. 7B is a graph showing Receiver Operating Characteristic (ROC) Curve Analysis of the Extra Trees algorithm.
Figure 7C:
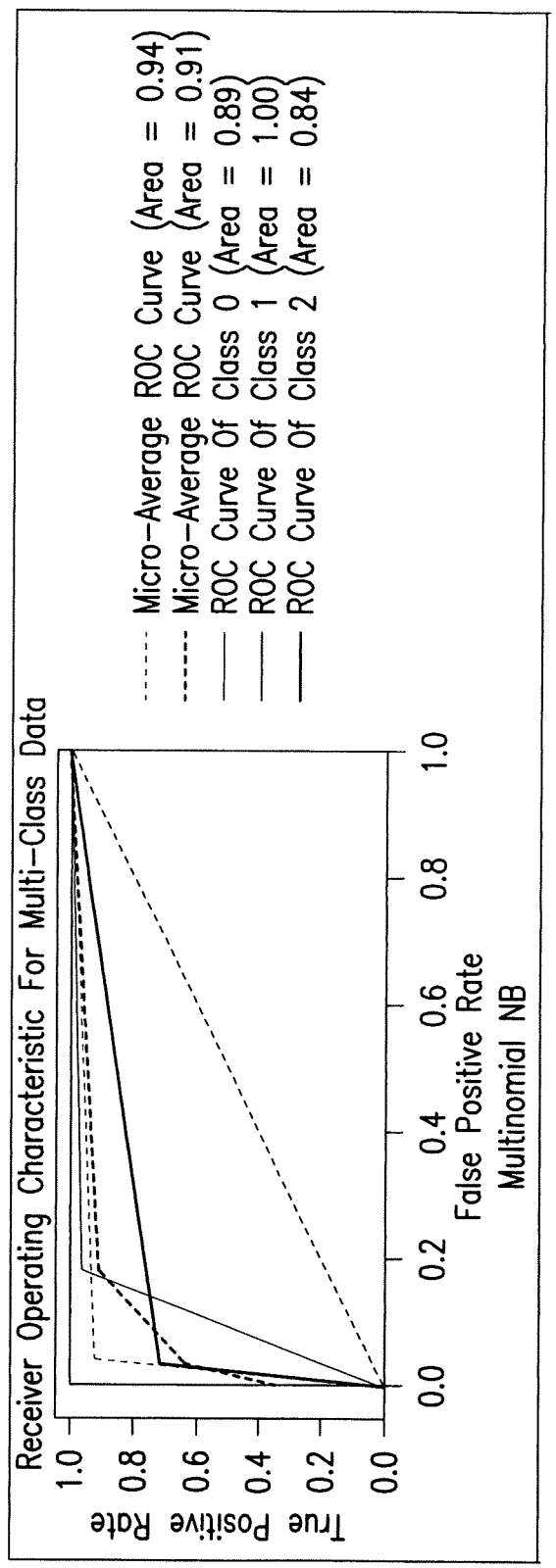
FIG. 7C is a graph showing Receiver Operating Characteristic (ROC) Curve Analysis of the Multinomial NB algorithm.
Figure 7D:
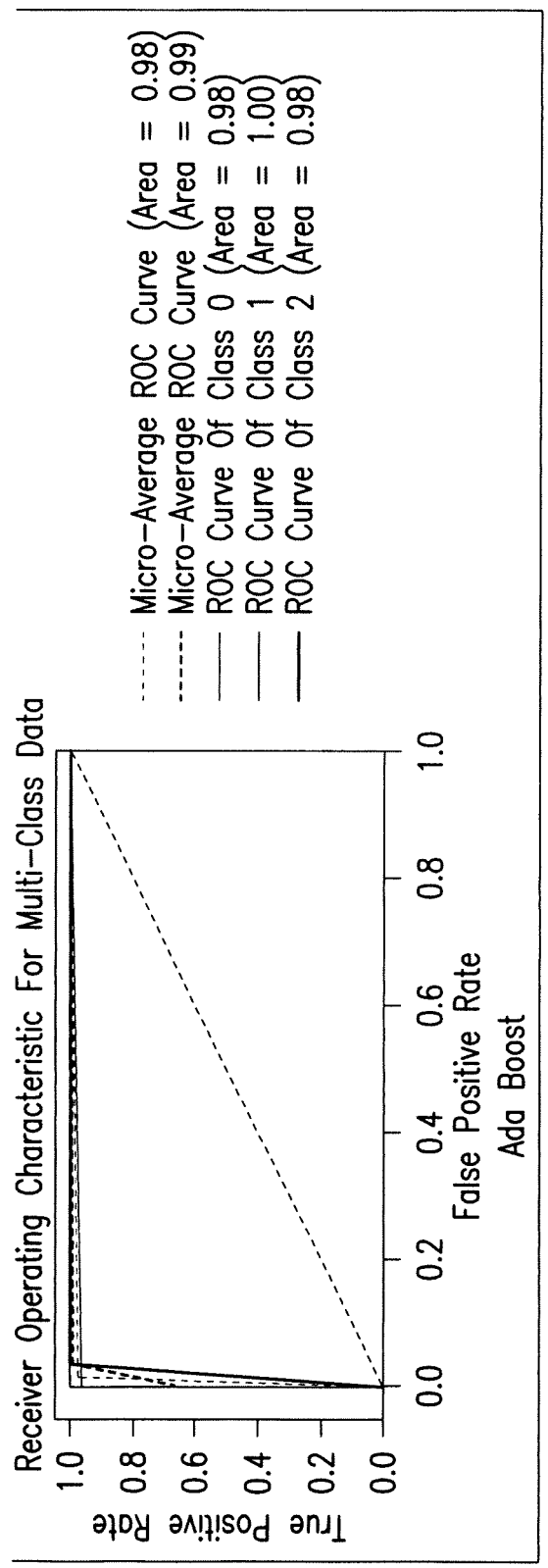
FIG. 7D is a graph showing Receiver Operating Characteristic (ROC) Curve Analysis of the Ada Boost algorithm.
Figure 7E:
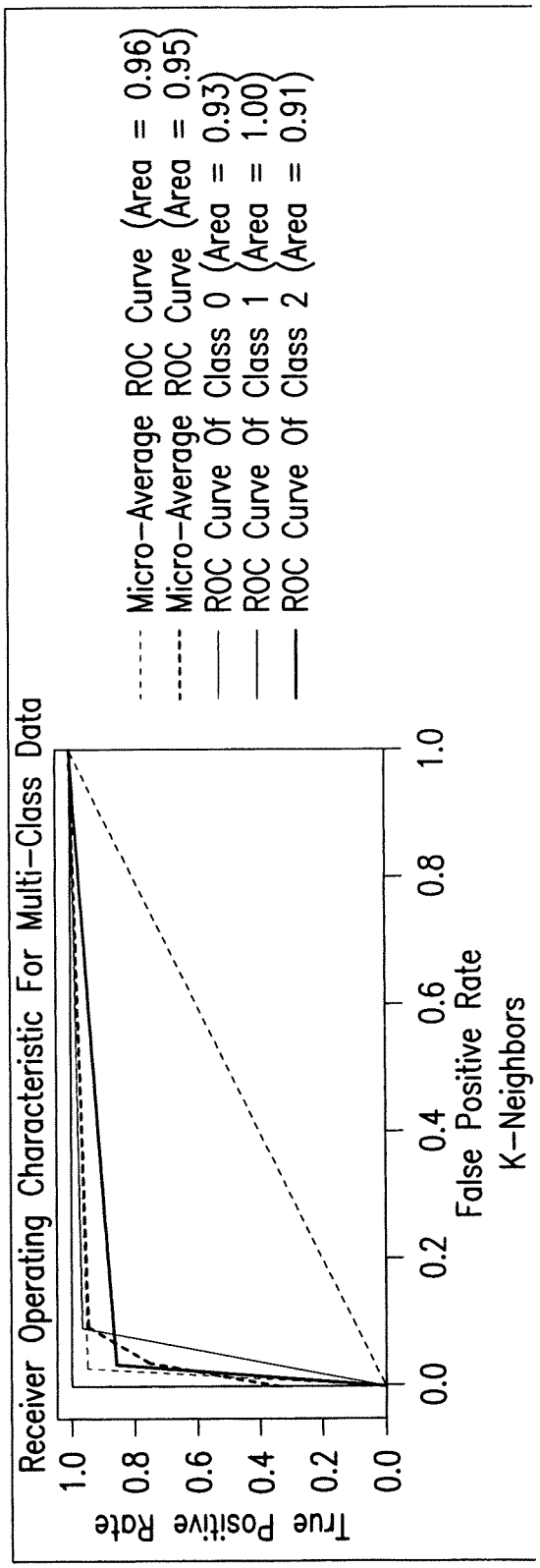
FIG. 7E is a graph showing Receiver Operating Characteristic (ROC) Curve Analysis of the K-Neighbors algorithm.
Figure 7F:
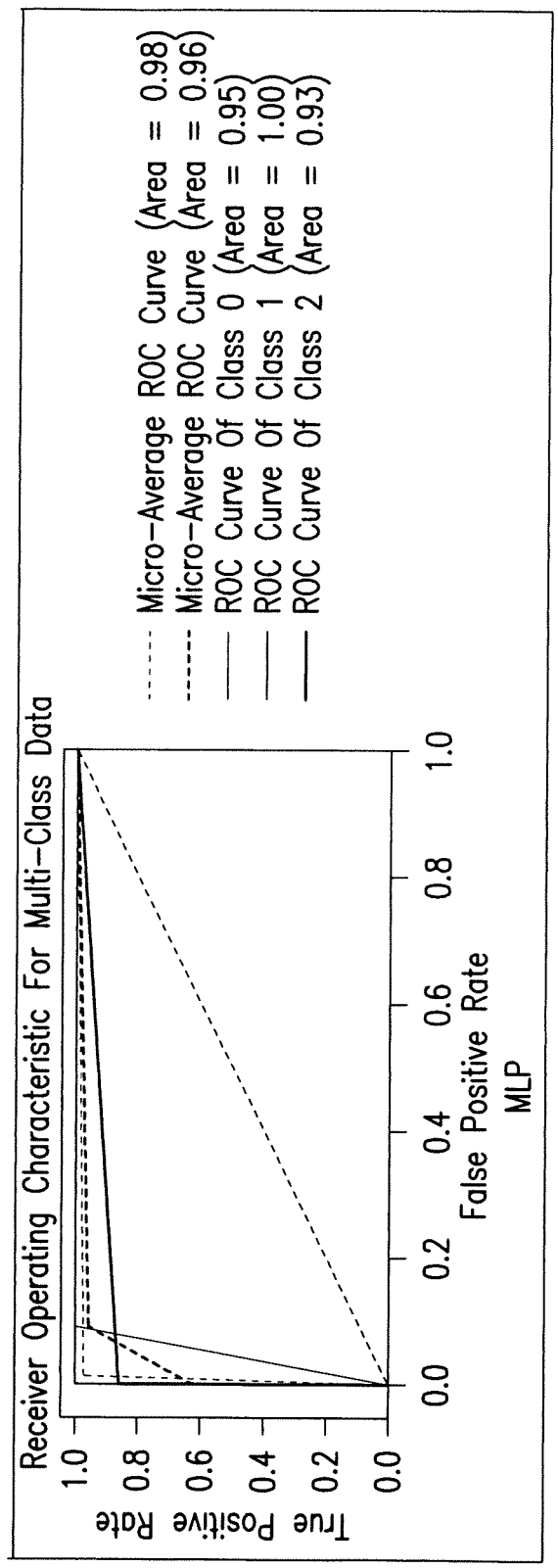
FIG. 7F is a graph showing Receiver Operating Characteristic (ROC) Curve Analysis of the MLP algorithm.
Figure 7G:
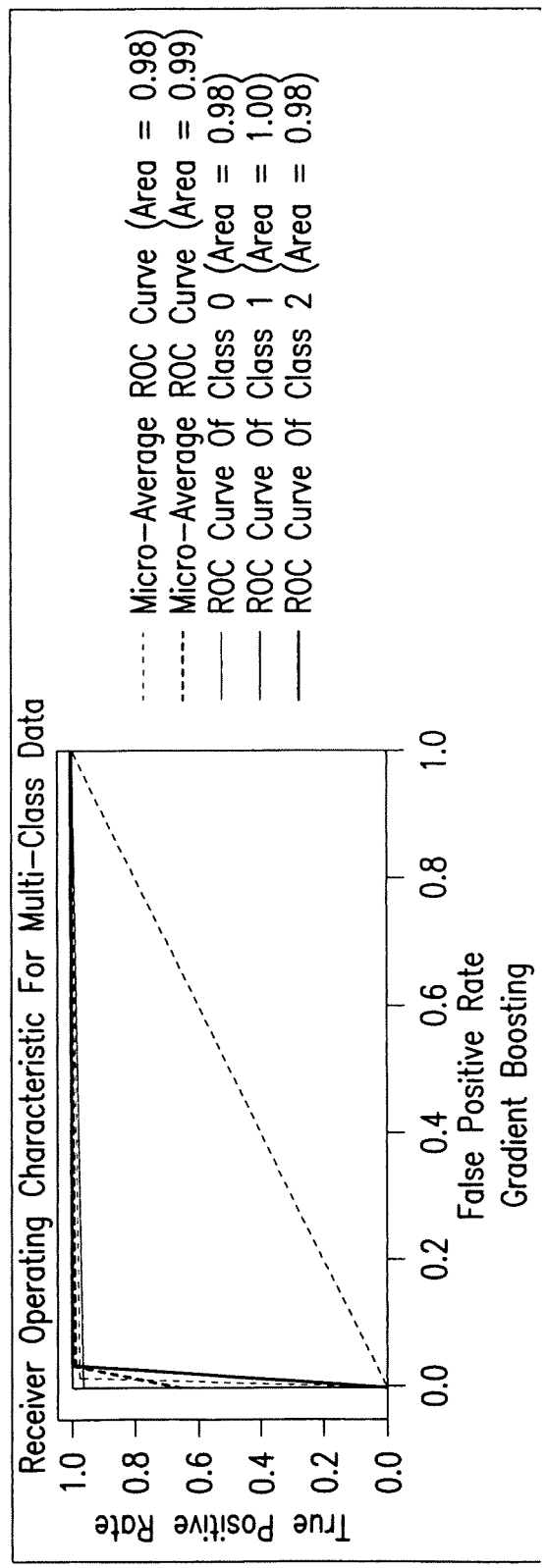
FIG. 7G is a graph showing Receiver Operating Characteristic (ROC) Curve Analysis of the Gradient Boosting algorithm.
Figure 7H:
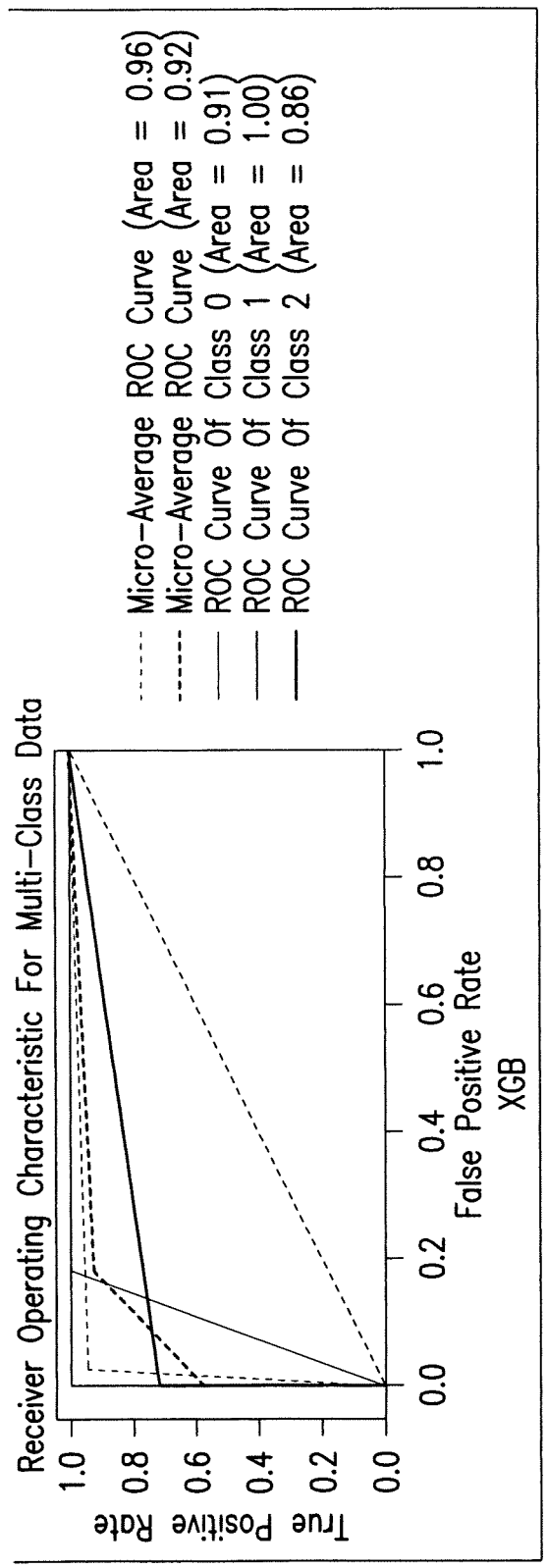
FIG. 7H is a graph showing Receiver Operating Characteristic (ROC) Curve Analysis of the XGB algorithm.
Figure 7I:
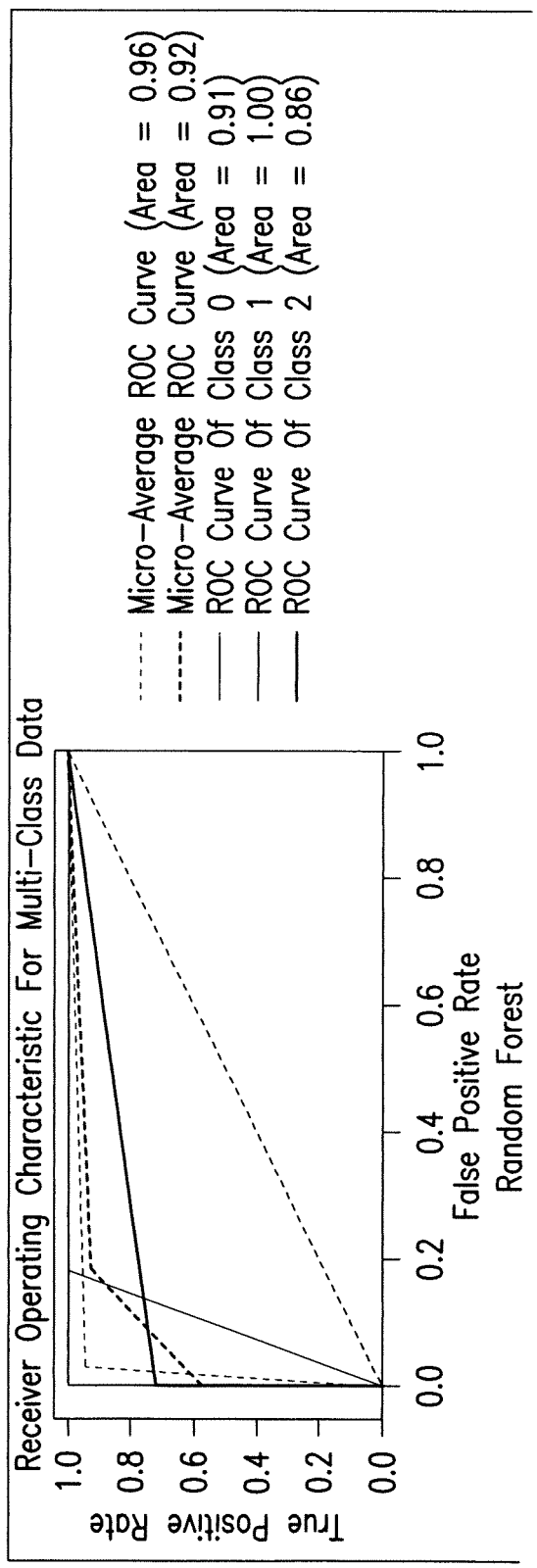
FIG. 7I is a graph showing Receiver Operating Characteristic (ROC) Curve Analysis of the RANDOM FOREST® algorithm.
Figure 7J:
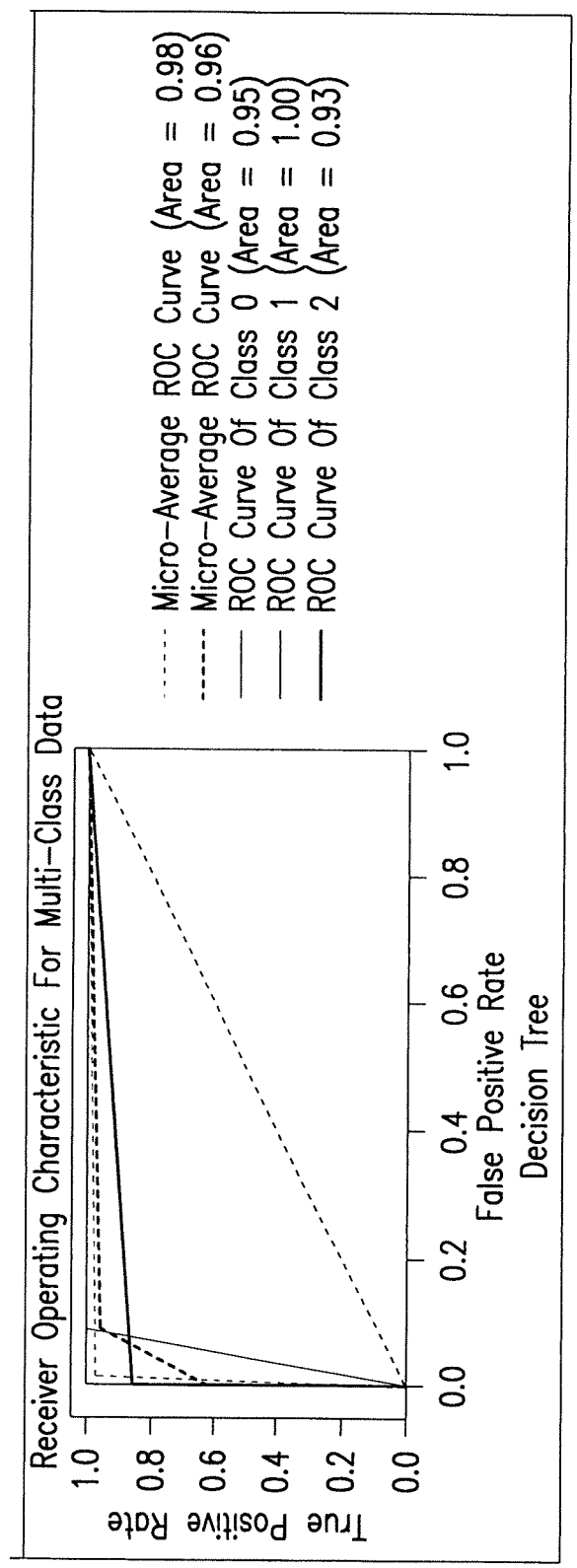
FIG. 7J is a graph showing Receiver Operating Characteristic (ROC) Curve Analysis of the Decision Tree algorithm.

The VR machine learning system aims to combine multiple pieces of evidence to arrive at one prediction by a voting approach such as majority voting. An embodiment of this invention employs an applied Ensemble Vote [43, 44] using all MLA methods that are mentioned above to get the accurate classification. This approach gives a better predictive performance compared to a single model. That is why ensemble methods placed first in many prestigious machine learning competitions. Ensemble methods are meta-algorithms that combine several machine learning techniques into one predictive model in order to decrease variance, bias, or improve predictions. when patients' data increases, using a single algorithm may give an opposite result or less accuracy and the result is inconsistent. Consequently, it is necessary to use the majority voting approach instead of choosing a single algorithm as a final result. Ensemble Vote is a list of classifiers that combine similar or different ML classifiers into a single model for classification via majority voting as shown in FIG. 5. After the voting-based ensemble model is constructed, it can be used to make a prediction on new data. Classification Voting Ensemble Predictions are the majority vote of contributing models where the latter classifiers could be implemented by two different techniques: hard and soft voting [44] [43]. Hard voting predicts the class label based on the most frequently used label by the classification models as equation (1), whereas soft voting predicts the class label based on averaging the class-probabilities as equation (2) [44].

$$Cx = \operatorname{argmax} i \sum_{j=1}^{B} I(hj(x) = i)$$

Where hj are given different classification rules, and i) is an indicator function [44]

$$Cx = \operatorname{argmax} i \sum_{j=1}^{B} pij$$

where pij is the probability estimate from the jth classification rule for cation rule for the ith class [44]

Performance Evaluation

As discussed above, we have used different MLAs that measured how accurately the ML algorithms classified patients into three classes: cognitive impairment (dementia), cognitively healthy and mild cognitive impairment.

Evaluation metrices such as sensitivity, specificity, accuracy, F1, precision, Mean Squared Error (MSE), ROC curve, Micro-average and Macro-average were used to determine the performance of ML models. The different MLAs that were used to measure the classification of patients included: Extra Trees, SVC, AdaBoost, K-Neighbors, XGB, Decision Tree, MLP, Multinomial NB, and RANDOM FOREST®. Below, training and testing phase will be explained, the performance results of MLAs and learning curve will be discussed in detail. After that, the results will be generalized by a voting approach, namely Ensemble Vote [43]. Visualization data is also described.

Training and Testing Phase

In the training phase, ten classifiers were used to train the data. The procedure starts from splitting the data into 70% training dataset and 30% testing dataset. Then, each approach builds its model (with a specific structure). After that, the models are tested to check their effectiveness using measures such as accuracy, sensitivity, specificity, MSE, F1, Micro-avg, Macro-avg and ROC curve.

Evaluation Performance of ML Model

After testing phase, different metrices were used to evaluate the performance of ML models: sensitivity, specificity, accuracy, F1, precision, ROC curve, MSE, Micro-average and Macro-average. The evaluation metrics were extracted from Confusion Matrix (CM) where the latter gives a summary of prediction results on a classification problem (see FIG. 6). This study calculated the evaluation metrics for each class of multi-categorical classification models (normal=0, demented=1, MCI=2) to understand the actual prediction results. Furthermore, CM has the actual # of classes and the predicted # of classes.

As shown in FIG. 6, the CM shows the numbers of False Negative (FN), False Positive (FP), True Negative (TN), and True Positive (TP) [48]. A True Positive (TP) is an outcome where the model correctly predicts the positive class, and a True Negative (TN) is an outcome where the model correctly predicts the negative class. In addition, a False Positive (FP) is an outcome where the model incorrectly predicts the positive class, and a False Negative (FN) is an outcome where the model incorrectly predicts the negative class. As it can be observed from FIG. 6:

TP for Dementia class in SVC=CM [1][1]=4,

FN for Dementia class in SVC=CM [1][0]+CM [1][2]=0,

TN for Dementia class in SVC=CM [0][0]+CM [2][2]+CM [0][2]+CM [2][0]=32,

FP for Dementia class in SVC=CM [0][1]+MC [2][1]=0.

The data below demonstrates that many models are satisfactory and that some models better than others at predicting which patients have dementia.

As shown in Table II, most of the algorithms have a high accuracy 97.22%, which means that most of the participants are assigned to the right class. The actual error rates, are suggested as performance measures for the classifications procedure. As shown in Table I, the actual error rate was between 11≤AER≤0.22 which is an acceptable misclassification rate. In the development of this invention, 10-fold cross validation procedures were used to train the data and to validate the model effectiveness well. Cross-validation is a technique which trains a particular set from the whole dataset, while it reserves the remaining data by splitting it into 10 folds. Then, it builds the model on 10 folds of the dataset. After the model is built, it is tested to check the effectiveness for the 10th fold. This procedure is repeated with the latter steps while recording the accuracy and errors until each of the ten folds has served as the test dataset. Performance metrics of the model were extracted from the average of k records. 10-fold cross validation procedures showed high values in all models. 10-fold cross validation procedures showed high values in all models where the data set is split into 10 folds. The highest percentage was 99.14% for RANDOM FOREST® as well as for Extra Trees as shown in Table II.

TABLE II

Evaluation Metrices to Determine the Performance of the Machine Learning Models

| Machine Learning Algorithms | Accuracy | Actual Error Rate (AER) | Cross Validation Accuracy |
|---|---|---|---|
| Extra Trees | 97.22% | 0.22 | 99.14% |
| AdaBoost | 97.22% | 0.11 | 97.43% |
| MLP | 97.22% | 0.22 | 96.58% |
| XGB | 94.44% | 0.22 | 97.43% |
| Decision Tree | 97.22% | 0.11 | 97.43% |
| Gradient Boosting | 97.22% | 0.11 | 98.29% |
| SVC | 97.22% | 0.11 | 98.29% |
| K-Neighbors | 94.44% | 0.22 | 89.74% |
| Random Forest | 94.44% | 0.22 | 99.14% |
| Multinomial NB | 91.66% | 0.33 | 85.47% |

Other metrics used in the development of this invention were sensitivity, specificity and precision. Sensitivity [49] is the proportion of true positives that are correctly identified by the test.

The sensitivity of cognitively healthy participants in all methods was between 0.96 to 1 (i.e.: 100%), which means that most of the cognitively healthy participants are predicted to be cognitively healthy. The sensitivity of dementia patients (as shown in Table III) is 100% for all models. In other words, the proportion of participants suffering from the disease who were correctly identified as the ones suffering from the disease is 100% for each of the models. Similarly, the sensitivity of cognitively impaired patients MCI is 100% in Extra Trees, AdaBoost as well as Gradient Boosting, whereas, the sensitivity of MCI was between 71% to 86% in the rest of models.

Specificity [49] aka recall, is the proportion of true negatives that are correctly identified by the test. The specificity of cognitively healthy participants is 100% in Extra Trees, AdaBoost as well as Gradient Boosting. Furthermore, the specificity of cognitively healthy participants in the rest of the models (as shown in Table III) is between 0.82≤specificity ≤0.91. The higher value of specificity refers to the lower proportion of participants who are unhealthy but got predicted as cognitively healthy [49]. Demented participants have a higher value of specificity equal to 1 in all models except Extra Trees which means no other classes than dementia patients were labeled as dementia class. Similarly, the specificity of MCI class was equal to 1 in most of the models, revealing that no cognitively healthy or demented patients were classified as MCI.

Precision [50] is the proportion of correctly predicted positive values against all the positive predictions. The higher the precision, the better. It helps when a model has very high precision. In contrast, if a model has low precision, that indicates false positives are high; this indicates there is a misdiagnosis. As it can be observed from Table III, the precision of cognitively healthy participants showed the perfect percentage 100% in AdaBoost, Extra Trees as well as Gradient Boosting, whereas the precision of cognitively healthy participants in rest of the MLAs ranged from 92% to 96%. Similarly, cognitively impaired patients showed the perfect percentage 100% precision in all models except Extra Tress (as shown in Table III). In the same way, the findings of precision showed high percentage in most of the models in MCI class.

TABLE III

Validation Metrices to Determine the Performance of the Machine Learning Models

| Machine Learning Algorithms | Precision | | | Sensitivity | | | Specificity | | |
| --- | --- | --- | --- | --- | --- | --- | --- | --- | --- |
| | Cog. Healthy | MCI | Dement. | Cog. Healthy | Dement. | MCI | Cog. Healthy | Dement. | MCI |
| Extra Trees | 1.00 | 0.80 | 1.00 | 0.96 | 1.00 | 1.00 | 1.00 | 0.97 | 1.00 |
| AdaBoost | 1.00 | 1.00 | 0.88 | 0.96 | 1.00 | 1.00 | 1.00 | 1.00 | 0.97 |
| MLP | 0.96 | 1.00 | 1.00 | 1.00 | 1.00 | 0.86 | 0.91 | 1.00 | 1.00 |
| XGB | 0.93 | 1.00 | 1.00 | 1.00 | 1.00 | 0.71 | 0.82 | 1.00 | 1.00 |
| Decision Tree | 0.96 | 1.00 | 1.00 | 1.00 | 1.00 | 0.86 | 0.91 | 1.00 | 1.00 |
| Gradient Boosting | 1.00 | 1.00 | 0.88 | 0.96 | 1.00 | 1.00 | 1.00 | 1.00 | 0.97 |
| SVC | 0.96 | 1.00 | 1.00 | 1.00 | 1.00 | 0.86 | 0.91 | 1.00 | 1.00 |
| K-Neighbors | 0.96 | 1.00 | 0.86 | 0.96 | 1.00 | 0.86 | 0.91 | 1.00 | 0.97 |
| Random Forest | 0.93 | 1.00 | 1.00 | 1.00 | 1.00 | 0.71 | 0.82 | 1.00 | 1.00 |
| Multinomial NB | 0.92 | 1.00 | 0.83 | 0.96 | 1.00 | 0.71 | 0.82 | 1.00 | 0.97 |

The F1-Scores are the equally weighted harmonic mean of recall and precision. F1-scores in all MLAs ranged from 94% to 98%. Demented patients showed the perfect percentage 100% for all models except Extra Trees. Similar to the precision and recall results in MCI class, F1 scores showed high-percentage in most of the models i.e. most of the models give high values between 83% to 100%.

When the system classifies multiple class labels, it looks for averaging evaluation measures to generalize the results. Further, in order to ensure that there is a range for the measurement of the various metrices, micro-average and macro-average were used to view the averaging evaluation measures on the general results. The micro-average method is a useful measurement and makes sense when the data size is variant. As shown in Table IV, Micro-avg of Recall, Precision and F1-Scores revealed an accuracy of 97% or 94% in all models except Multinomial NB model. In a multi-class setting, micro-averaged precision and recall are always the same. Therefore, each model has the same accuracy micro-avg of Recall, Precision and F1-scores. Macro-average metrics are used to assess the system performance across variance datasets. So, the values of Macro-average F1-Score ranging from 91% to 97% indicate that the models have a high performance in classifying multiple class labels, depending on averaging evaluation measures.

TABLE IV

Micro-avg and Macro-avg Metrices To Determine the Performance of The Machine Learning Models

| | | Recall | | Precision | | F1-score | | |
| --- | --- | --- | --- | --- | --- | --- | --- | --- |
| MLA | Classes | Micro avg | Macro avg | Micro avg | Macro avg | F1-score | Micro avg | Macro avg |
| Extra Trees | Healthy | 0.97 | 0.99 | 0.93 | 0.99 | 0.98 | 0.97 | 0.96 |
| | Dementia | | | | | 0.89 | | |
| | MCI | | | | | 1.00 | | |
| AdaBoost | Healthy | 0.97 | 0.95 | 0.97 | 0.99 | 0.98 | 0.97 | 0.97 |
| | Dementia | | | | | 1.00 | | |
| | MCI | | | | | 0.92 | | |
| MLP | Healthy | 0.97 | 0.95 | 0.97 | 0.99 | 0.98 | 0.97 | 0.97 |
| | Dementia | | | | | 1.00 | | |
| | MCI | | | | | 0.92 | | |
| XGB | Healthy | 0.94 | 0.90 | 0.94 | .980 | 0.96 | .94 | 0.93 |
| | Dementia | | | | | 1.00 | | |
| | MCI | | | | | 0.83 | | |
| Decision Tree | Healthy | 0.97 | 0.95 | 0.97 | 0.99 | 0.98 | 0.97 | 0.97 |
| | Dementia | | | | | 1.00 | | |
| | MCI | | | | | 0.92 | | |
| Gradient Boosting | Healthy | 0.97 | 0.95 | 0.97 | 0.99 | 0.98 | 0.97 | 0.97 |
| | Dementia | | | | | 1.00 | | |
| | MCI | | | | | 0.92 | | |
| SVC | Healthy | 0.97 | 0.95 | 0.97 | 0.99 | 0.98 | 0.97 | 0.97 |
| | Dementia | | | | | 1.00 | | |
| | MCI | | | | | 0.92 | | |
| KNeighbors | Healthy | 0.94 | 0.94 | 0.94 | 0.94 | 0.96 | 0.94 | 0.94 |
| | Dementia | | | | | 1.00 | | |
| | MCI | | | | | 0.86 | | |
| Random Forest | Healthy | 0.94 | 0.90 | 0.94 | .980 | 0.96 | 0.94 | 0.93 |
| | Dementia | | | | | 1.00 | | |

Receiver Operating Characteristic (ROC) curve for multiclass data measures the accuracy of rating and diagnostic test results. It is used to determine the optimal cut-off value which generates a curve in the unit square. ROC curve is a graphical plot for multiclass data which measures the accuracy of rating and illustrates the diagnostic test results. It is created by plotting the true positive rate (TPR) against the false positive rate (FPR) at various threshold settings [51]. The minimum acceptable value of area under the curve should be 0.5 [51]. As it can be observed from FIG. 7, the ROC curve of demented patients' class is perfectly equal to 1 in all models except Extra trees. Similarly, the ROC curve in the MCI' class is perfect, equal to 1.00 in Extra Trees. Furthermore, Ada Boost, Gradient Boosting, SVC, MLP as well as Decision Tree are located progressively closer to the upper left-hand corner in ROC space with the value being equal to 0.93 or 0.98, which means the performance reflects the status of diagnostic disease that gives high prediction. Furthermore, Micro-avg ROC curve revealed high performance in all models, with values ranging between 94% and 98%. In the same way, Macro-avg ROC curve revealed performance between 91% and 99%. This concluded that the ROC curve of demented patients' class has a greater discrimination capacity than other classes and there is no overlap between them. Overall, the results of the ROC curve were very satisfactory and showed perfect values in disease classification.

As a conclusion, all evaluation metrices used to determine the performance of the ML models revealed that there is a high level of classification accuracy, sensitivity, specificity, precision, F1, ROC curve, Micro-Avg, Macro-Avg. Furthermore, the highest performance rate according to rank assessed from the SVC, MLP, AdaBoost, Extra Trees, Gradient Boosting, and Decision Tree showed that there is no distinction between them.

Generalize MLA Results Using Voting Approach

Figure 8:
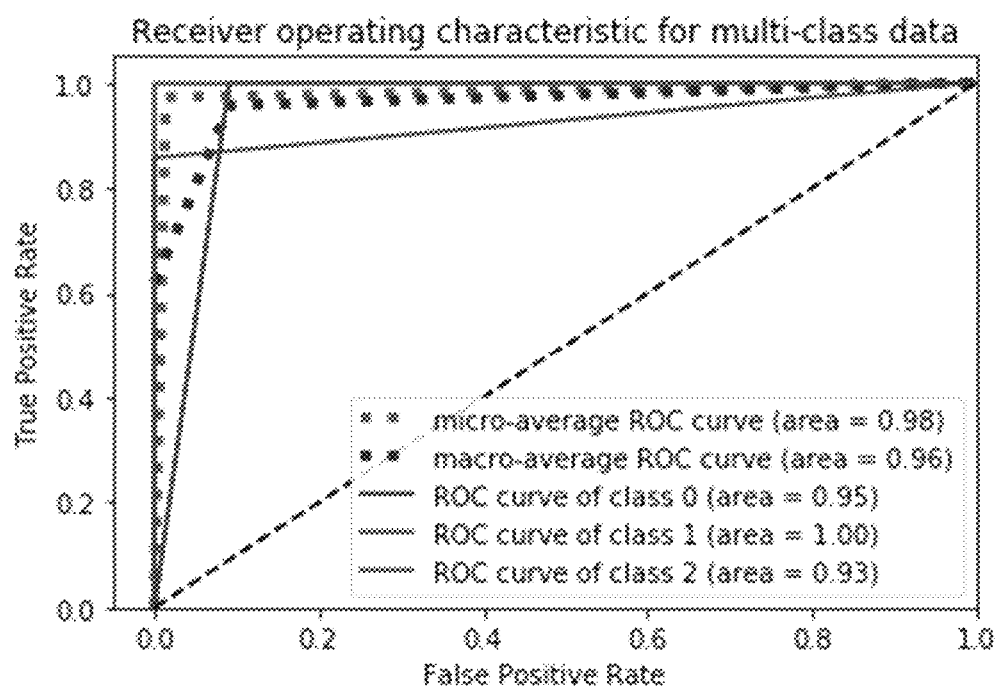
FIG. 8 is a graph showing an ROC Curve Analysis of Ensemble Vote.

Table V shows the performance results after the voting approach by hard vote method and all different classifiers have equal weight where the accuracy of classification is 97.22%, sensitivity of dementia patients and cognitively healthy are 100% whereas the sensitivity of MCI is 86%. Specificity and precision of dementia patients and MCI patients are 100%. As shown in FIG. 8, Micro-avg ROC curve and Macro-avg ROC curve is closed to 1. Furthermore, ROC curve for all classes shows high values between 0.93 and 1.00.

TABLE V

Evaluation Metrices To Determine the Performance by Majority Voting

| | Voting Algorithm (Ensemble Vote) | | |
| --- | --- | --- | --- |
| Metrices | Cog. Healthy | Dement. | MCI |
| Precision | 0.96 | 1.00 | 1.00 |
| Sensitivity | 1.00 | 1.00 | 0.86 |
| Specificity | 0.91 | 1.00 | 1.00 |
| F1-Score | 0.98 | 1.00 | 0.92 |
| ROC-Curve | 0.95 | 1.00 | 0.93 |
| Micro-avg ROC curve | 0.98 | | |
| Macro-avg ROC curve | 0.96 | | |
| Accuracy | 97.22% | | |
| AER | 0.11 | | |

As can be seen from the above, a comparison of the classification accuracy of all participants using traditional clinical diagnosis method vs. the VR+machine learning system has been made. The dementia diagnosis at clinic (expert diagnosis) depends on functional evaluation plus a cognitive test such as Mini-Cog test at early stages of disease. As noted above, it was observed that patients' classification at clinic—which depended on the Mini-Cog test with functional evaluation—showed 94% accuracy, whereas VR system combined with navigational ability showed 97.22% using Majority Voting approach described herein.

Overall, the highest performance was derived from Ensemble Vote with value equal to 97.22%, which confirms the reliability of the system. In addition, demented patients' class has a greater discriminate capacity than other classes where all performance results equal to 1. This led to the conclusion that there is no overlap between them.

Today, disease diagnosis is an important task. Computers play a vital role as a decision support system in the diseases diagnostic test. This invention combines a model for patient information storage and retrieval, cognitive test-based VR System and ML for classifying the patients' cognitive impairment. The system contains four basic tests with specific tasks. Each task consists of an assessment of a human cognitive field. The system evaluates two human cognitive domains: memory, and visuospatial function. Machine learning algorithms were used to classify patients into three classes: cognitive impairment (dementia), cognitively healthy and mild cognitive impairment. The system relies on a plurality of algorithms where a vote is made between them to choose the correct classification by using Ensemble Vote approach. The example above describes the use of ten algorithms; however, smaller and larger numbers can be employed (e.g., 3-15 algorithms; 3-8 algorithms, 5-10 algorithms; 5-12 algorithms, 8-11 algorithms, etc.).

This virtual reality machine learning platform offers many advantages compared to other more traditional cognitive assessment systems: it is easier and more ecologically valid, and requires less time and resource consumption. Moreover, it evaluates more than one cognitive field to give accuracy in evaluation. This system is unique as it relies on MLA to classify patients. The findings presented herein reveal that many and perhaps all machine learning algorithms have high level of predictions, specificity, precision and sensitivity. In addition, while the findings show low percentage in a few of the models in MCI class, because the sample number of MCI class was very small compared to other groups.

All evaluation metrices used to determine the performance of the machine learning models revealed that there is a high level of accuracy in the classification of patients. Furthermore, the highest performance rated according to rank assessed 97.22% accuracy from the SVC, MLP, Ada-Boost, Extra Trees, Gradient Boosting, and Decision Tree showed that there is no distinction between them. Accordingly, after majority voting, the highest performance was derived from Ensemble Vote equal to 97.22%, which confirms reliability of system test. Moreover, the ROC curve of demented patients' class has a greater discriminate capacity than other classes and there is no overlap between them.

ACKNOWLEDGEMENTS

This project was funded by the Deanship of Scientific Research (DSR), King Abdulaziz University, Jeddah, Saudi Arabia under grant no. (KEP-Msc-7-611-38). The authors, therefore, acknowledge with thanks DSR technical and financial support. IRB approval was from Unit of Biomedical Ethics Research Committee under Reference No 535-18-KAU, Dr. Soliman Fakeeh Hospital) DSFH (Policy No GLD-025 under (48/IRB/2019), and from research center of International Medical Centre (IMC) under IMC-IRB #2019-03-104. The authors of this article would like to thank Mr. Abdulrahman Ali and Eng. Mazen Alquliti for their valuable suggestions and helpful comments.

REFERENCES

1. Geldmacher, D. S. and P. J. Whitehouse, Evaluation of dementia. New England Journal of Medicine, 1996. 335 (5): p. 330-336.
2. Alzheimer's, A., 2015 Alzheimer's disease facts and figures. Alzheimer's & dementia: the journal of the Alzheimer's Association, 2015. 11(3): p. 332.
3. Montenegro, J. M. F. and V. Argyriou, Cognitive evaluation for the diagnosis of Alzheimer's disease based on Turing Test and Virtual Environments. Physiology & Behavior, 2017. 173: p. 42-51.
4. Lau, H.-C., et al., Non-invasive screening for Alzheimer's disease by sensing salivary sugar using Drosophila cells expressing gustatory receptor (Gr5a) immobilized on an extended gate ion-sensitive field-effect transistor (EG-ISFET) biosensor. PloS one, 2015. 10(2): p. e0117810.
5. Akgul, C. B. and A. Ekin. A Probabilistic Information Fusion Approach to MR-based Automated Diagnosis of Dementia. in Pattern Recognition (ICPR), 2010 20th International Conference on. 2010. IEEE.
6. Han, S. D., et al., Beta amyloid, tau, neuroimaging, and cognition: sequence modeling of biomarkers for Alzheimer's Disease. Brain imaging and behavior, 2012. 6(4): p. 610-620.
7. Cruz-Oliver, D. M., et al., Cognitive deficit reversal as shown by changes in the Veterans Affairs Saint Louis University Mental Status (SLUMS) examination scores 7.5 years later. Journal of the American Medical Directors Association, 2014. 15(9): p. 687. e5-687. e10.
8. Yeh, S.-C., et al. An innovative virtual reality system for mild cognitive impairment: diagnosis and evaluation. in Biomedical Engineering and Sciences (IECBES), 2012 IEEE EMBS Conference on. 2012. IEEE.
9. Tarnanas, I., et al., Ecological validity of virtual reality daily living activities screening for early dementia: longitudinal study. JMIR Serious Games, 2013. 1(1): p. el.
10. Yamada, E., et al., Assessment and care of visuospatial disorientation in a mixed dementia patient: a case study using objective measurements. Psychogeriatrics, 2016. 16(4): p. 277-282.
11. Salimi, S., et al., Can visuospatial measures improve the diagnosis of Alzheimer's disease? Alzheimer's & Dementia: Diagnosis, Assessment & Disease Monitoring, 2017.
12. Tu, S., et al., Lost in spatial translation-A novel tool to objectively assess spatial disorientation in Alzheimer's disease and frontotemporal dementia. Cortex, 2015. 67: p. 83-94.
13. Pal, A., et al., Study of visuospatial skill in patients with dementia. Annals of Indian Academy of Neurology, 2016. 19(1): p. 83.
14. Mohr, E., et al., Selective deficits in Alzheimer and Parkinsonian dementia: visuospatial function. Canadian Journal of Neurological Sciences, 1990. 17(3): p. 292-297.
15. Frisch, S., et al., Dissociating memory networks in early Alzheimer's disease and frontotemporal lobar degeneration-a combined study of hypometabolism and atrophy. PloS one, 2013. 8(2): p. e55251.
16. Park, J. H., et al., Memory performance on the story recall test and prediction of cognitive dysfunction progression in mild cognitive impairment and Alzheimer's dementia. Geriatrics & gerontology international, 2016.

17. Cordell, C. B., et al., Alzheimer's Association recommendations for operationalizing the  detection of cognitive impairment during the Medicare Annual Wellness Visit in a primary care setting. Alzheimer's & Dementia: The Journal of the Alzheimer's Association, 2013. 9(2): p. 141-150.
18. Ellis, S. R., What are virtual environments? IEEE Computer Graphics and Applications, 1994. 14(1): p. 17-22.
19. Weakley, A., et al., Neuropsychological test selection for cognitive impairment classification: A machine learning approach. Journal of Clinical & Experimental Neuropsychology, 2015. 37(9): p. 899-916.
20. Cushman, L. A., K. Stein, and C. J. Duffy, Detecting navigational deficits in cognitive aging and Alzheimer disease using virtual reality. Neurology, 2008. 71(12): p. 888-895.
21. Zakzanis, K. K., et al., Age and dementia related differences in spatial navigation within an immersive virtual environment. Medical Science Monitor, 2009. 15(4): p. CR140-CR150.
22. Lesk, V. E., et al., Using a virtual environment to assess cognition in the elderly. Virtual Reality, 2014. 18(4): p. 271-279.
23. Plancher, G., et al., Using virtual reality to characterize episodic memory profiles in amnestic mild cognitive impairment and Alzheimer's disease: influence of active and passive encoding. Neuropsychologia, 2012. 50(5): p. 592-602.
24. Shamsuddin, S. N. W., et al. VREAD: a virtual simulation to investigate cognitive function in the elderly. in Cyberworids (CW), 2012 International Conference on. 2012. IEEE.
25. Fatima, M. and M. Pasha, Survey of machine learning algorithms for disease diagnostic. Journal of Intelligent Learning Systems and Applications, 2017. 9(01): p. 1.
26. Abdullah, M., et al., A novel adaptive e-learning model matching educator-student learning styles based on machine learning. 2017.
27. Kononenko, I., Machine learning for medical diagnosis: History, state of the art and perspective. Artificial intelligence in medicine, 2001. 23: p. 89-109.
28. Yeh, S.-C., et al., Machine learning-based assessment tool for imbalance and vestibular dysfunction with virtual reality rehabilitation system. Computer methods and programs in biomedicine, 2014. 116(3): p. 311-318.
29. Lezak, M., D. Howieson, and D. Loring, Neuropsychological assessment. 5th edn Oxford University Press. Oxford, New York, ISBN, 2012. 10: p. 9780195395525.
30. Allain, P., et al., Detecting everyday action deficits in Alzheimer's disease using a nonimmersive virtual reality kitchen. Journal of the International Neuropsychological Society, 2014. 20(05): p. 468-477.
31. Sathya, R. and A. Abraham, Comparison of supervised and unsupervised learning algorithms for pattern classification. Int J Adv Res Artificial Intell, 2013. 2(2): p. 34-38.
32. Kaur, G. and A. Chhabra, Improved J48 Classification Algorithm for the Prediction of Diabetes. International Journal of Computer Applications, 2014. 98(22).
33. Geurts, P., D. Ernst, and L. Wehenkel, Extremely randomized trees. Machine learning, 2006. 63(1): p. 3-42.
34. Freund, Y. and R. E. Schapire, A decision-theoretic generalization of on-line learning and an application to boosting. Journal of computer and system sciences, 1997. 55(1): p. 119-139.
35. Chen, T. and C. Guestrin. Xgboost: A scalable tree boosting system. in Proceedings of the 22nd acm sigkdd international conference on knowledge discovery and data mining. 2016. ACM.
36. Ridgeway, G., The state of boosting. Computing Science and Statistics, 1999: p. 172-181.
37. Satyanarayana, N., C. Ramalingaswamy, and Y. Ramadevi, Survey of Classification Techniques in Data Mining.
38. Pumpuang, P., A. Srivihok, and P. Praneetpolgrang. Comparisons of classifier algorithms: Bayesian network, C4.5, decision forest and NBTree for Course Registration Planning model of undergraduate students. in Systems, Man and Cybernetics, 2008. SMC 2008. IEEE International Conference on. 2008.
39. McCallum, A. and K. Nigam. A comparison of event models for naive bayes text classification. in AAAI-98 workshop on learning for text categorization. 1998. Citeseer.
40. Nurnberger, A., C. Borgelt, and A. Klose. Improving naive Bayes classifiers using neuro-fuzzy learning. in Neural Information Processing, 1999. Proceedings. ICONIP '99. 6th International Conference on. 1999.
41. Grother, P. J., G. T. Candela, and J. L. Blue, Fast implementations of nearest neighbor classifiers. Pattern Recognition, 1997. 30(3): p. 459-465.
42. Windeatt, T., Ensemble MLP classifier design, in Computational Intelligence Paradigms. 2008, Springer. p. 133-147.
43. Pedregosa, F. a. V., G. and Gramfort, A. and Michel, V., et al., Scikit-learn: Machine Learning in {P}ython. Journal of Machine Learning Research, 2011. 12: p. 2825-2830.
44. James, G., Majority vote classifiers: theory and applications. 1998.
45. Korting, T. S., C4. 5 algorithm and multivariate decision trees. Image Processing Division, National Institute for Space Research-INPE Sao Jose dos Campos-SP, Brazil, 2006.
46. Van Essen, B., et al. Accelerating a random forest classifier: Multi-core, GP-GPU, or FPGA? in 2012 IEEE 20th International Symposium on Field-Programmable Custom Computing Machines. 2012. IEEE.
47. Pugazhenthi, D. and S. Rajagopalan, Machine learning technique approaches in drug discovery, design and development. Information Technology Journal, 2007. 6(5): p. 718-724.
48. Manliguez, C., Generalized Confusion Matrix for Multiple Classes. 2016.
49. Altman, D. G. and J. M. Bland, Diagnostic tests. 1: Sensitivity and specificity. BMJ: British Medical Journal, 1994. 308(6943): p. 1552.
50. Vafeiadis, T., et al., A comparison of machine learning techniques for customer churn prediction. Simulation Modelling Practice and Theory, 2015. 55: p. 1-9.
51. Hajian-Tilaki, K., Receiver Operating Characteristic (ROC) Curve Analysis for Medical Diagnostic Test Evaluation. Caspian journal of internal medicine, 2013. 4(2): p. 627-635.

The invention claimed is:
1. A visuospatial disorders detection method, comprising:
presenting to a subject a three dimensional (3D) virtual reality environment in which the subject utilizes a multidirectional input device to input answers to questions and to guide an avatar on a path through the 3D virtual reality environment, wherein said multidirectional input device at least moves front, back, left and right;

receiving input data for the subject generated by the subject's use of the multidirectional input device which comprises answers to questions input by the subject, coordinates and direction of the avatar relative to the path through the 3D virtual reality environment, and a time period used by the subject to guide the avatar along the path through the 3D virtual reality environment;

supplying the received input data into a plurality of machine learning algorithms which utilizes correct and incorrect answers input by the subject, number of changes in direction of the avatar as the subject moves the avatar relative to the path through the 3D virtual reality environment, and the time period used by the subject to guide the avatar along the path through the 3D virtual reality environment, wherein the plurality of machine learning algorithms comprise Decision Tree Classifier, Extra Tree Classifier, AdaBoost Classifier, XGB Classifier, Gradient Boosting Classifier, Support Vector Classifier, Random Forest Classifier, Multinomial Naive Bayes, K-Neighbors Classifier, and Multilayer Perceptron;

using machine learning with each of the plurality of machine learning algorithms to classify the subject into one of three classification labels selected from the group consisting of normal, demented, and mild cognitive impairment; and feeding results obtained with each of the plurality of machine learning algorithms into a system of voting to produce a final classification, wherein the system of voting comprises hard voting which predicts the final classification based on a most frequently used classification label produced by the machine learning using the plurality of machine learning algorithms.

2. The method of claim 1 wherein the input data received from the subject answering questions and guiding the avatar relative to the path through the 3D virtual reality environment represent testing of both memory and visuospatial function.

3. The method of claim 1 wherein the input data received from the subject answering questions and guiding the avatar relative to the path through the 3D virtual reality environment represent testing of each of navigation, visual memory, and memory function.

4. A visuospatial disorders detection method, comprising:
presenting to a subject a three dimensional (3D) virtual reality environment in which the subject utilizes a multidirectional input device to input answers to questions and to guide an avatar on a path through the 3D virtual reality environment;

receiving input data for the subject generated by the subject's use of the multidirectional input device which comprises answers to questions input by the subject, coordinates and direction of the avatar relative to the path through the 3D virtual reality environment, and a time period used by the subject to guide the avatar along the path through the 3D virtual reality environment;

supplying the received input data into a plurality of machine learning algorithms which utilizes correct and incorrect answers input by the subject, number of changes in direction of the avatar as the subject moves the avatar relative to the path through the 3D virtual reality environment, and the time period used by the subject to guide the avatar along the path through the 3D virtual reality environment, wherein the plurality of machine learning algorithms comprise Decision Tree Classifier, Extra Tree Classifier, AdaBoost Classifier, XGB Classifier, Gradient Boosting Classifier, Support Vector Classifier, Random Forest Classifier, Multinomial Naive Bayes, K-Neighbors Classifier, and Multilayer Perceptron;

using machine learning with each of the plurality of machine learning algorithms to classify the subject into one of three classification labels selected from the group consisting of normal, demented, and mild cognitive impairment; and feeding results obtained with each of the plurality of machine learning algorithms into a system of voting to produce a final classification, wherein the system of voting comprises soft voting which predicts the final classification based on averaging classification labels produced by the machine learning using the plurality of machine learning algorithms.

5. The method of claim 4 wherein the input data received from the subject answering questions and guiding the avatar relative to the path through the 3D virtual reality environment represent testing of both memory and visuospatial function.

6. The method of claim 4 wherein the input data received from the subject answering questions and guiding the avatar relative to the path through the 3D virtual reality environment represent testing of each of navigation, visual memory, and memory function.

* * * * *